(12) United States Patent
Nakamura et al.

(10) Patent No.: US 8,236,844 B2
(45) Date of Patent: Aug. 7, 2012

(54) HISTIDINE DERIVATIVES

(75) Inventors: Ko Nakamura, Hyogo (JP); Yoshitaka Nakazawa, Hyogo (JP); Minoru Kawamura, Hyogo (JP); Kunihiko Higashiura, Hyogo (JP); Tomoshi Miura, Hyogo (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 497 days.

(21) Appl. No.: 12/087,591

(22) PCT Filed: Jan. 23, 2007

(86) PCT No.: PCT/JP2007/050942
§ 371 (c)(1),
(2), (4) Date: Oct. 15, 2008

(87) PCT Pub. No.: WO2007/086354
PCT Pub. Date: Aug. 2, 2007

(65) Prior Publication Data
US 2009/0149658 A1    Jun. 11, 2009

(30) Foreign Application Priority Data
Jan. 24, 2006   (JP) ................. 2006-014656

(51) Int. Cl.
C07D 233/64 (2006.01)
A61K 31/4172 (2006.01)
(52) U.S. Cl. .................... 514/400; 548/338.1
(58) Field of Classification Search ............ 548/338.1
See application file for complete search history.

(56) References Cited

U.S. PATENT DOCUMENTS

2002/0150629 A1  10/2002  Nishimura et al.
2009/0149658 A1  6/2009   Nakamura et al.

FOREIGN PATENT DOCUMENTS

| EP | 0 127 076 A2 | 12/1984 |
| JP | A-59-216597 | 12/1984 |
| JP | 06-041411 B | 6/1994 |
| JP | A-07-097323 | 4/1995 |
| JP | A-09-020660 | 1/1997 |
| JP | A-09-020661 | 1/1997 |
| JP | A-10-298197 | 11/1998 |
| JP | 2939301 B | 6/1999 |
| JP | A-2003-267992 | 9/2003 |
| JP | A-2006-232685 | 9/2006 |
| WO | WO 01/091762 | 12/2001 |
| WO | WO 2007/086354 A1 | 8/2007 |

OTHER PUBLICATIONS

Bentolila et al. J. Med. Chem. 2000, 43, 2591-2600.*
Zhao et al. Eur. J. Med. Chem. 1993, 28, 949-954.*
Vippagunta et al. Advanced Drug Delivery Reviews, 48 (2001), pp. 3-26.*
Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Ohkubo et al.; "Catalytic activities of novel L-histidyl group-introduced polymers imprinted by a transition state analogue in the hydrolysis of amino acid esters;" Journal of Molecular Catalysis A: Chemical; 1995; pp. L111-L114; vol. 101.
Bentolila et al.; "Poly(N-acryl amino acids): A New Class of Biologically Active Polyanions;" Journal of Medical Chemistry; 2000; pp. 2591-2600; vol. 43.
Cho et al.; "Hydrophobic and Ionic Interactions in the Ester Hydrolysis by Imidazole-Containing Polymers;" Bulletin of Korean Chemical Society; 1982; 34-36; vol. 3, No. 1.
Zhao et al.; "New agents for cutaneous photoprotection: derivatives of α-amino acids, 4-aminobenzoic and 4-methoxycinnamic acids;" European Journal of Medical Chemistry; 1993; pp. 949-954; vol. 28.
Office Action issued in U.S. Appl. No. 12/452,533 on Feb. 29, 2012.
Oct. 8, 2010 Office Action issued in U.S. Appl. No. 12/452,533.
U.S. Appl. No. 12/087,591, filed Oct. 15, 2008 to Nakamura et al. commonly assigned to Nippon Zoki Pharmaceutical Company.
Garipcan et al., "A Novel Affinity Support Material for the Separaion of Immunoglobulin G From Human Plasma," Macromol. Biosci. 2002, pp. 135-144, vol. 2.

(Continued)

Primary Examiner — Joseph Kosack
Assistant Examiner — Matthew Coughlin
(74) Attorney, Agent, or Firm — Oliff & Berridge, PLC

(57) ABSTRACT

A novel histidine derivative represented by the following formula (I), and a pharmaceutically acceptable salt and hydrate thereof, useful as a pharmaceutical agent such as analgesics for the treatment of various kinds of acute or chronic pain diseases and of neuropathic pain diseases:

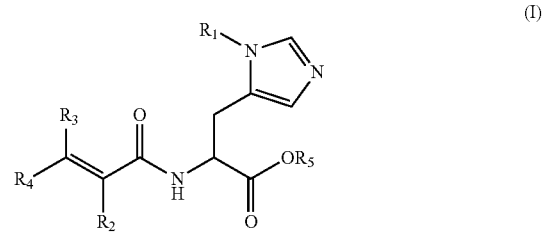

(I)

wherein, $R_1$ is hydrogen, alkyl having 1 to 6 carbon(s) or benzyl which may be substituted with alkyl having 1 to 4 carbon(s) or halogen; $R_2$ is hydrogen or alkyl having 1 to 4 carbon(s); $R_3$ and $R_4$ are same or different and each is hydrogen, alkyl having 1 to 4 carbon(s) or phenyl which may be substituted with any one or two of alkyl having 1 to 6 carbon(s), alkoxy having 1 to 6 carbon(s), halogen, trifluoromethyl, nitro and cyano; and $R_5$ is hydrogen or an alkyl group having 1 to 4 carbon(s).

17 Claims, No Drawings

OTHER PUBLICATIONS

Aug. 19, 2008 International Search Report issued in International Application No. PCT/JP2008/063046 (with translation).

Kita et al., Nippon Yakurigaku Zasshi, "Stress state caused by alteration of rhythm in environmental temperature, and the functional disorders in mice and rats," Folia pharmacol.japon, 1975, pp. 195-210, vol. 71 (with Abstract).

Kita et al., Tail Pressure Method, "Analgesic effects of Neurotropin in mice, and comparison between analgesic effects of some drugs in SART-stress mice and normal mice," Nippon Yakurigaku Zasshi, Folia pharmacol.japon, 1976, pp. 573-584, vol. 72 (with Abstract).

Kim et al., "An experimental model for peripheral neuropathy produced by segmental spinal nerve ligation in the rat," Pain, 1992, pp. 355-363, vol. 50.

Lee et al., "Receptor Subtype Mediaing the Adrenergic Sensitivity of Pain Behavior and Ectopic Discharges in Neuropathic Lewis Rats," J. Neurophysiol., 1999, pp. 2226-2233, vol. 81.

Chaplan et al., "Quantitative assessment of tactile allodynia in the rat paw," Journal of Neuroscience Methods, 1994, pp. 55-63, vol. 53.

May 26, 2011 Office Action issued in U.S. Appl. No. 12/452,533.

\* cited by examiner

HISTIDINE DERIVATIVES

CROSS-REFERENCE TO RELATED APPLICATIONS

This is a National Stage of PCT Application No. PCT/JP2007/050942 filed Jan. 23, 2007, which claims the benefit of Japanese Application No. JP2006-014656 filed Jan. 24, 2006.

BACKGROUND

The present invention relates to a novel histidine derivative and a pharmaceutically acceptable salt and hydrate thereof and also to a pharmaceutical agent containing said compound as an effective ingredient.

Anserine (N-β-alanyl-1-methyl-L-histidine) or carnosine (β-ananyl-L-histidine) in which β-alanine is bonded to histidine or methylhistidine, respectively is a histidine derivative abundantly available in muscles of mammals, birds, reptiles, amphibian, etc. and has been reported to have various pharmacological actions.

For example, it has been disclosed that anserine has an immunomodulating action (refer to Patent Document 1) and an anti-stress action (refer to Patent Document 2) and that anserine and carnosine have a suppressive action for hypertension (refer to Patent Document 3), a promoting action for iron absorption (refer to Patent Document 4), an enhancing action for learning ability (refer to Patent Document 5), a promoting action for zinc absorption (refer to Patent Document 6) and antioxidant/anti-aging/anti-cancer actions (refer to Patent Document 7). However, there has been no report for their analgesic action.

Patent Document 1: Japanese Examined Patent Publication No. Hei-06/041,411
Patent Document 2: Japanese Patent Laid-Open No. Hei-09/020,660
Patent Document 3: Japanese Patent No. 2,939,301
Patent Document 4: Japanese Patent Laid-Open No. Hei-07/097,323
Patent Document 5: Japanese Patent Laid-Open No. Hei-09/020,661
Patent Document 6: International Publication WO 01/091,762
Patent Document 7: Japanese Patent Laid-Open No. 2003/267,992

SUMMARY

An object of the present invention is to provide a novel compound which is useful as an excellent analgesic agent.

The present inventors have carried out intensive studies for the compounds which are effective for various types of pains and, as a result, they have found that a novel histidine derivative represented by the following formula (I) shows an excellent analgesic action in pathogenic model animals suffering from acute or chronic pain and neuropathic pain and is useful as a pharmaceutical agent whereupon the present invention has been accomplished.

The histidine derivative of the present invention is a novel compound showing an excellent analgesic action to pathogenic model animals suffering from acute or chronic pain and neuropathic pain and is a lowly toxic compound showing no abnormal finding at all in the toxicity tests. Accordingly, the compound of the present invention is very useful as a pharmaceutical agent such as an analgesic for the treatment of diseases exhibiting acute or chronic pain and neuropathic pain.

DETAILED DESCRIPTION

The present invention relates to a histidine derivative represented by the following formula (I) and a pharmaceutically acceptable salt and hydrate thereof and also to a pharmaceutical agent such as an analgesic containing said compound as an effective ingredient.

[chem. 1]

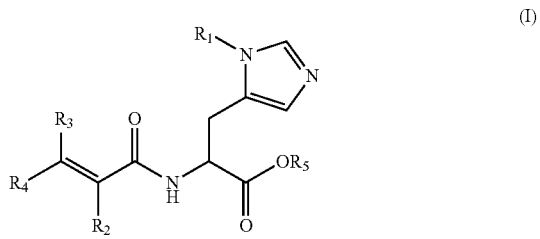

(I)

In the formula, $R_1$ is hydrogen, alkyl having 1 to 6 carbon(s) or benzyl which may be substituted with alkyl having 1 to 4 carbon(s) or halogen; $R_2$ is hydrogen or alkyl having 1 to 4 carbon(s); $R_3$ and $R_4$ are same or different and each is hydrogen, alkyl having 1 to 4 carbon(s) or phenyl which may be substituted with any one or two of alkyl having 1 to 6 carbon(s), alkoxy having 1 to 6 carbon(s), halogen, trifluoromethyl, nitro and cyano; and $R_5$ is hydrogen or an alkyl group having 1 to 4 carbon(s).

In the substituent for the above formula (I), alkyl having 1 to 6 carbon(s) is preferably a linear or branched alkyl group such as methyl, ethyl, propyl, isopropyl, butyl, isobutyl, sec-butyl, tert-butyl, pentyl, isopentyl, neopentyl, tert-pentyl, hexyl and isohexyl, and alkyl having 1 to 4 carbon(s) is preferably a linear or branched alkyl group such as methyl, ethyl, propyl, isopropyl, butyl, isobutyl, sec-butyl and tert-butyl.

Alkoxy having 1 to 6 carbon(s) is preferably a linear or branched alkoxy group such as methoxy, ethoxy, propyloxy, isopropyloxy, butyloxy, pentyloxy and hexyloxy.

Halogen is fluoro, chloro, bromo, iodo, etc.

Preferred compounds of the present invention are the following ones and ester thereof (the compounds which $R_5$ is an alkyl group having 1 to 4 carbon(s) in the above formula (I)).

N(α)-acryloyl-N(π)-methyl-L-histidine [Compound 1]
N(α)-acryloyl-N(π)-ethyl-L-histidine [Compound 2]
N(α)-crotonoyl-N(π)-methyl-L-histidine [Compound 3]
N(α)-crotonoyl-N(π)-ethyl-L-histidine [Compound 4]
N(α)-3-methylcrotonoyl-N(π)-methyl-L-histidine [Compound 5]
N(α)-3-phenylpropenoyl-N(π)-methyl-L-histidine [Compound 6]
N(π)-2-methyl-2-butenoyl-N(π)-methyl-L-histidine [Compound 7]
N(α)-acryoyl-N(π)-propyl-L-histidine [Compound 8]
N(π)-3-methylcrotonoyl-N(π)-ethyl-L-histidine [Compound 9]
N(π)-3-phenylpropenoyl-N(π)-ethyl-L-histidine [Compound 10]
N(π)-2-methyl-2-butenoyl-N(π)-ethyl-L-histidine [Compound 11]
N(α)-crotonoyl-N(π)-propyl-L-histidine [Compound 12]

N(α)-acryloyl-N(π)-isopropyl-L-histidine [Compound 13]
N(α)-acryloyl-L-histidine [Compound 14]
N(α)-acryloyl-N(π)-methyl-D-histidine [Compound 15]
N(π)-3-(4-methylphenyl)acryloyl-N(π)-methyl-L-histidine [Compound 16]
N(π)-3-(4-methoxyphenyl)acryloyl-N(π)-methyl-L-histidine [Compound 17]
N(π)-3-(4-chlorophenyl)acryloyl-N(π)-methyl-L-histidine [Compound 18]
N(π)-3-(3,4-dichlorophenyl)acryloyl-N(π)-methyl-L-histidine [Compound 19]
N(π)-3-(4-fluorophenyl)acryloyl-N(π)-methyl-L-histidine [Compound 20]
N(π)-3-(3,5-bistrifluoromethylphenyl)-acryloyl-N(π)-methyl-L-histidine [Compound 21]
N(α)-3-(4-isobutylphenyl)-acryloyl-N(π)-methyl-L-histidine [Compound 22]
N(α)-3-(3,4-dimethoxyphenyl)acryloyl-N(π)-methyl-L-histidine [Compound 23]
N(α)-3-(4-nitrophenyl)acryloyl-N(π)-methyl-L-histidine [Compound 24]
N(α)-3-(3-cyanophenyl)acryloyl-N(π)-methyl-L-histidine [Compound 25]
N(α)-3-(3-methoxyphenyl)acryloyl-N(π)-methyl-L-histidine [Compound 26]
N(α)-acryloyl-N(π)-benzyl-L-histidine [Compound 27]
N(α)-acryloyl-N(π)-4-chlorobenzyl-L-histidine [Compound 28]
N(α)-acryloyl-N(π)-4-methylbenzyl-L-histidine [Compound 29]
N(α)-methacryl-N(π)-methyl-L-histidine [Compound 30]

As hereunder, a general process for producing the compound of the present invention will be shown. The compound of the present invention represented by the above formula (I) is a histidine derivative in which an alkyl group or hydrogen is on a n-nitrogen atom of an imidazole ring and is able to be produced by the process mentioned below. As hereunder, examples of a process for producing an L-substance of the histidine derivative which is the compound of the present invention will be shown and a D-substance which is a stereoisomer thereof is also able to be synthesized by the same route.

(1) In case $R_1$ is an alkyl group

In order to selectively alkylate the π-position of imidazole of histidine, synthesis was carried out according to the route shown by the following [chem. 2] using N-Boc-L-histidine methyl ester as a starting substance according to a method mentioned in the literature (Brown, J. H. Jones and J. D. Richards, *J. Chem. Soc. Perkin Trans.* I, page 1533, 1982).

(A) was treated with trityl chloride in methylene chloride in the presence of triethylamine to give a τ-trityl substance (B). In methylene chloride, (B) was heated to reflux with 10 molar equivalents of alkyl iodide to give an ammonium salt (C).

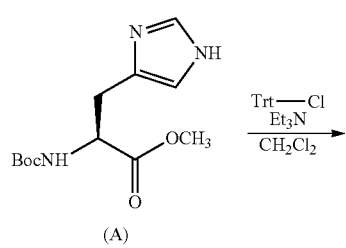

(A)

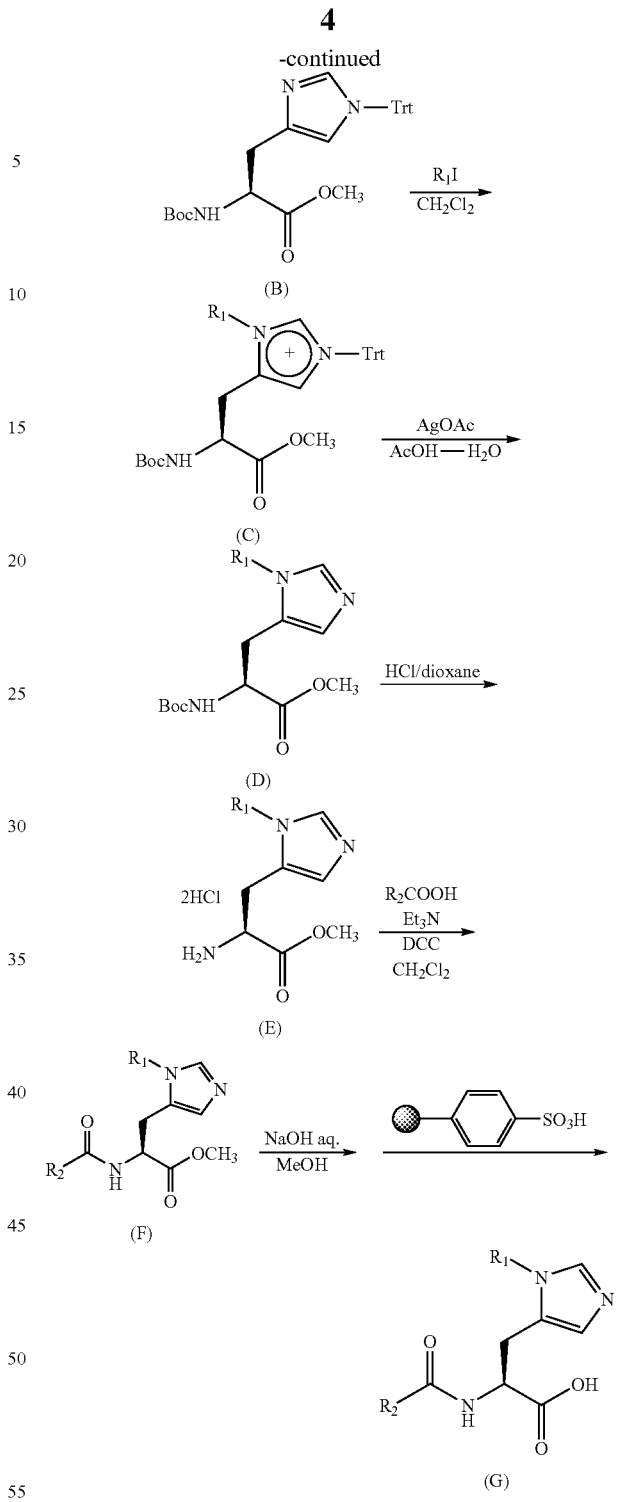

(C) was further treated with silver acetate in 80% acetic acid to convert into a compound (D). The Boc group of (D) was removed by hydrogen chloride/dioxane and the resulting hydrochloride (E) was condensed with a carboxylic acid using dicyclohexyl carbodiimide (DCC) to give (F).

After finishing the reaction, DCUrea which was insoluble in methylene chloride was filtered off and the filtrate was purified by a silica gel column chromatograph to isolate (F). Thus, firstly, silica gel of a type where an aminopropyl group was modified was used and triethylamine hydrochloride was degraded with an aminopropyl group, hydrogen chloride was adsorbed with the silica gel, free triethylamine was eluted and triethylamine was removed by means of vacuum distillation. Further, unreacted DCC, etc. were removed using common silica gel to give (F) in a high purity.

A methyl ester of (F) was removed by saponifying with an alkali in methanol and sodium ion was removed by a polystyrene-carrying sulfonic acid to give a free acid (G). (G) was made into an amorphous solid by means of freeze-drying to give the final product.

(2) In case $R_1$ is hydrogen

As shown in the following [chem. 3], histidine methyl ester dihydrochloride (H) was treated with acrylic acid chloride in methylene chloride in the presence of triethylamine to give (I). Methyl ester of (I) was removed by an alkaline saponification in methanol while sodium ion was removed by polystyrene-carrying sulfonic acid to give a free acid (J). (J) was made into an amorphous solid by freeze-drying to give the final product.

[chem. 3]

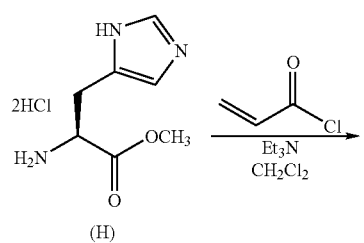

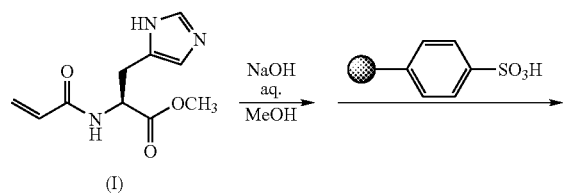

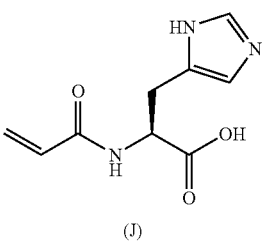

(3) In case $R_1$ is an unsubstituted or substituted benzyl group

In the same manner as in the case where $R_1$ is an alkyl group, in order to selectively benzylate the n-position of imidazole of histidine, the compound (B) shown in [chem. 2] was used as a starting substance and synthesis was carried out by the route as shown in the following [chem. 4].

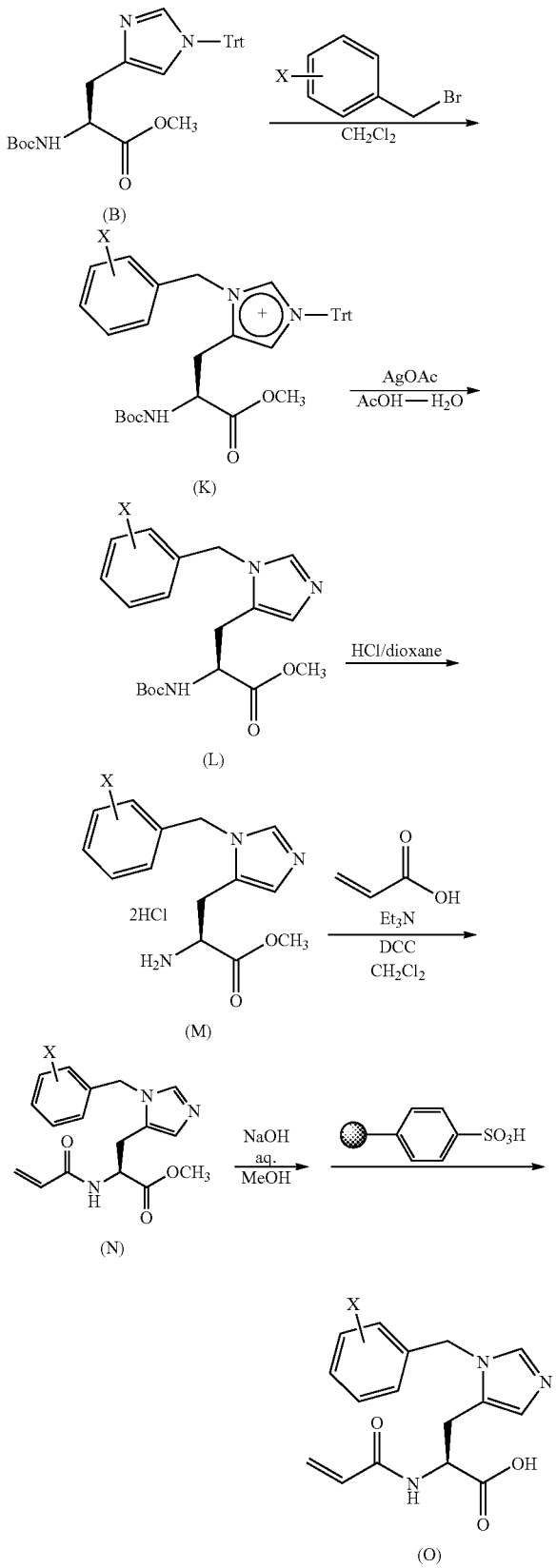

X = H, alkyl, halogen

A τ-trityl compound (B) produced in [chem. 2] was heated to reflux in methylene chloride with an excessive amount of benzyl bromide where the benzene ring was unsubstituted or the benzene ring had a substituent to give an ammonium salt (K). Then (K) was further treated with silver acetate in 80% acetic acid to convert it into a compound (L). Boc group of (L) was removed by hydrogen chloride/dioxane to give a hydrochloride (M). (M) was condensed with an acrylic acid using dicyclohexylcarbodiimide (DCC). After finishing the reaction, DCUrea which was insoluble in methylene chloride was filtered off and the filtrate was purified by a silica gel column chromatography to isolate (N). Methyl ester of (N) was removed by an alkaline saponification in methanol and sodium ion was removed by a polystyrene-carrying sulfonic acid to give a free acid (O). (O) was made into an amorphous solid by means of freeze-drying or was crystallized by ether to give the final product.

(4) In case $R_2$ is 2-(substituted phenyl)ethenyl group

In the same manner as in case where $R_1$ was an alkyl group, the compound (E) shown in [chem. 2] was used as a starting substance and synthesis was carried out by the route shown in the following [chem. 5].

The π-alkyl substance (E) produced in [chem. 2] was made to react with cinnamic acid chloride having various substituent on an aromatic ring in methylene chloride in the presence of triethylamine. After finishing the reaction, the reaction mixture was washed with water and purified by a silica gel column chromatography to isolate (P). Methyl ester of (P) was removed by an alkaline saponification in methanol, sodium ion was removed by a polystyrene-carrying sulfonic acid, the solvent was evaporated and crystallization was conducted using ether to give the final product (Q).

The compounds represented by the above-given formula (I) include the pharmaceutically acceptable salts of thereof such as acid addition salts with hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid or sulfanilic acid; salts with alkali metal such as sodium or potassium, salts with alkaline-earth metal such as calcium or magnesium, or salts with other metals such as aluminum; or salts with bases such as ammonia or organic amines. Those salts may be manufactured by known methods from the compounds of the present invention in a free state or may be mutually converted among the salts. When the steric isomers such as cis-trans isomer, optical isomer and conformational isomer, or hydrate and metal complexes of the substances of the present invention exist, the present invention includes any and all of them.

[chem. 5]

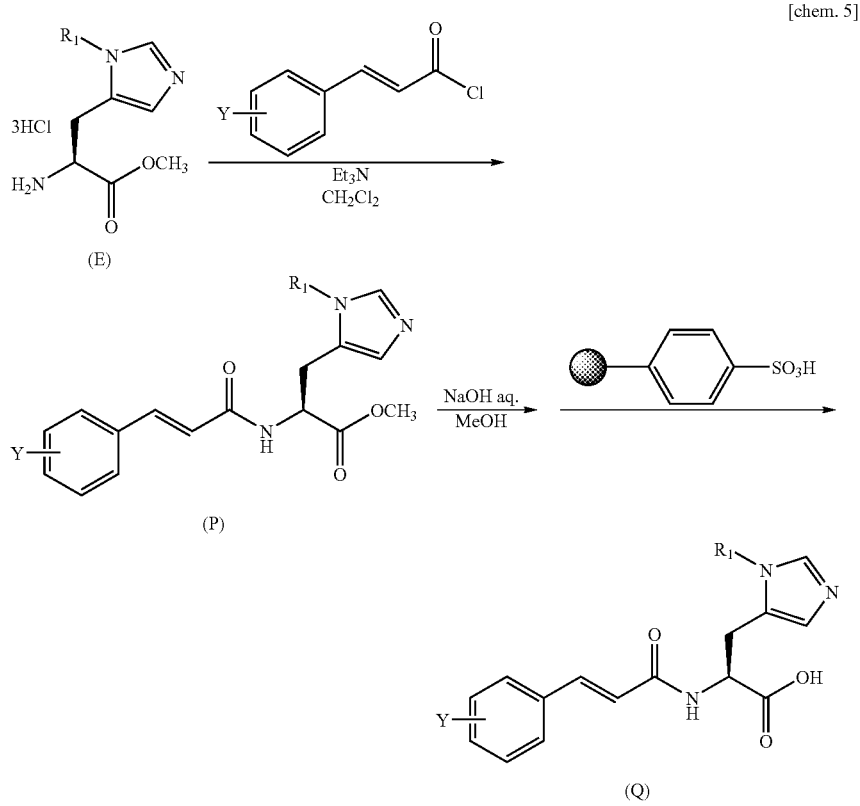

Y = alkyl, alkoxy, halogen, trifluoromethyl, nitro, cyano

The compound of the present invention can be made into pharmaceutical preparations by a combination with a suitable pharmaceutical carriers or diluents according to any conventional methods, for example, preparations for oral administrations (e.g. tablets, capsules, powders, liquids, etc.) and for parenteral administrations (e.g. for subcutaneous, intravenous, intramuscular, intrarectal and intranasal administrations). At preparing, the compound of the present invention may also be used in the form of the pharmaceutically acceptable salt, and can be used either solely or jointly together with other pharmaceutically effective ingredients.

The preferred dose of the compound of the present invention may vary depending upon the object to be administered the patient, form of the preparation, method for the administration, term for the administration, etc. and, in order to achieve a desired effect, 0.5-1000 mg per day may be usually given to common adults by oral route either once daily or several times a day. In the case of a parenteral administration such as by injection, a level of from 1/3 to 1/10 of the above-given dose by oral route is preferred.

EXAMPLES

Melting point was measured by a melting point measuring device of Yamato MP-21 type and was not corrected. Nuclear magnetic resonance spectrum ($^1$H-NMR) was measured by a nuclear magnetic resonance device of Bruker ARC-500 type and TMS ($\delta$=0) was used as an internal standard. Optical rotation was measured by a polarimeter of JASCO DP-140 type. A silica gel column chromatography was carried out using silica gel DM 1020 for chromatography of an aminopropyl group bonding type and silica gel BW-127ZH for common normal phase chromatography (both manufactured by Fuji Silicia K. K.). In a thin layer chromatography, Silica gel F254 (Merck, No. 5715) was used and detection was conducted using a UV lamp and a 5% phosphomolybdic acid-ethanol color reagent. With regard to the reagents and the solvents, commercially available ones were used just as they were.

Example 1

Production of N($\alpha$)-tert-butoxycarbonyl-N($\tau$)-triphenylmethyl-L-histidine methyl ester (B)

Boc-L-histidine methyl ester (A) (25.0 g, 93 mmol) and triethylamine (14 mL, 100 mmol) were dissolved in methylene chloride (400 mL) and cooled with ice and a solution of trityl chloride (27.9 g, 100 mmol) in methylene chloride (100 mL) was dropped thereinto during 30 minutes. After stirring under ice cooling for 30 minutes and at room temperature for 20 hours, the reaction mixture was washed with water and a saturated saline solution. After the organic layer was dried over anhydrous sodium sulfate, the solvent was evaporated in vacuo to give N($\alpha$)-tert-butoxycarbonyl-N($\tau$)-triphenylmethyl-L-histidine methyl ester (67.5 g, quantitatively) as an oily product. This was used for the next reaction just as it was.
$^1$H-NMR (DMSO-d$_6$) $\delta$: 1.34 (s, 9H), 2.73-2.84 (m, 2H), 3.55 (s, 3H), 4.19-4.24 (m, 1H), 6.66 (s, 1H), 7.03-7.07 (m, 7H), 7.10 (d, J=8.0 Hz, 1H), 7.28 (s, 1H), 7.35-7.42 (m, 9H).

Example 2

Production of 4-(2-tert-butoxycarbonylamino-2-methoxycarbonylethyl)-3-methyl-1-trityl-3H-imidazolyl-1-ium iodide N($\alpha$)-tert-butoxycarbonyl-N($\tau$)-triphenylmethyl-L-histidine methyl ester (93 mmol) was dissolved in methylene chloride (400 mL) and methyl iodide (56 mL, 900 mmol) was added thereto followed by heating to reflux for 20 hours on an oil bath (temperature: 55° C.). After being allowed to cool, the solvent was evaporated in vacuo and the oily residue was solidified from petroleum ether to give 4-(2-tert-butoxycarbonylamino-2-methoxycarbonylethyl)-3-methyl-1-trityl-3H-imidazolyl-1-ium iodide (58.0 g, 95%) as a yellow solid.

Mp. 178-179° C. $^1$H-NMR (DMSO-d$_6$) $\delta$: 1.32 (s, 9H), 2.98 (dd, J=9.5, 15.5 Hz, 1H), 3.14 (dd, J=5.0, 15.5 Hz, 1H), 3.62 (s, 3H), 3.80 (s, 3H), 4.36-4.42 (m, 1H), 7.11-7.15 (m, 6H), 7.28 (s, 1H), 7.42-7.48 (m, 10H), 8.96 (s, 1H).

Example 3

Production of N($\alpha$)-tert-butoxycarbonyl-N($\pi$)-methyl-L-histidine methyl ester 4-(2-tert-Butoxycarbonylamino-2-methoxycarbonylethyl)-3-methyl-1-trityl-3H-imidazolyl-1-ium iodide (58.0 g, 88.7 mmol) and silver acetate (15.0 g, 90 mmol) were added to 80% acetic acid (300 mL) followed by stirring for 20 hours at room temperature. After filtering off the insoluble matters, the solvent was evaporated in vacuo. The residue was dissolved in water and made alkaline by addition of anhydrous potassium carbonate and the oily product separated out therefrom was extracted with ethyl acetate. After the organic layer was dried over anhydrous sodium sulfate, the solvent was evaporated in vacuo. The oily residue was purified by a silica gel column chromatograph (chloroform:methnol=19:1) to give N($\alpha$)-tert-butoxycarbonyl-N($\pi$)-methyl-L-histidine methyl ester (18.94 g, 75%) as crystals.

Mp. 109-110° C. $[\alpha]_D^{20}$=□13.5° (c1, MeOH). $^1$H-NMR (DMSO-d$_6$) $\delta$: 1.35 (s, 9H), 2.87 (dd, J=9.8, 15.4 Hz, 1H), 2.97 (dd, J=4.2, 15.4 Hz, 1H), 3.53 (s, 3H), 3.62 (s, 3H), 4.18-4.25 (m, 1H), 6.64 (s, 1H), 7.33 (d, J=8.1 Hz, 1H), 7.48 (s, 1H).

Example 4

Production of N($\alpha$)-tert-butoxycarbonyl-N($\pi$)-ethyl-L-histidine methyl ester N($\alpha$)-tert-butoxycarbonyl-N($\tau$)-triphenylmethyl-L-histidine methyl ester (48.6 g, 95 mmol) was dissolved in methylene chloride (400 mL) and ethyl iodide (72 mL, 900 mmol) was added thereto followed by heating to reflux for 48 hours on an oil bath (temperature: 55° C.). Ethyl iodide (72 mL, 900 mmol) was further added thereto, the mixture was heated to reflux for 48 hours more and the solvent was evaporated in vacuo. Petroleum ether was added to the resulting oily residue, the mixture was subjected to a decantation for three times and dissolved in 80% acetic acid and then silver acetate (16.69 g, 100 mmol) was added thereto followed by stirring for 24 hours at room temperature. After the insoluble matters were filtered off, the solvent was evaporated in vacuo. The residue was dissolved in water and made alkaline by addition of anhydrous potassium carbonate and the oily product separated out therefrom was extracted with ethyl acetate. After the organic layer was dried over anhydrous sodium sulfate, the solvent was evaporated in vacuo. The oily residue was purified by a silica gel column chromatography (chloroform:methanol=19:1) to give N($\alpha$)-tert-butoxycarbonyl-N($\pi$)-ethyl-L-histidine methyl ester as an oily product.
$^1$H-NMR (DMSO-d$_6$) $\delta$: 1.29 (t, J=7.2 Hz, 3H), 1.35 (s, 9H), 2.87 (dd, J=9.8, 15.4 Hz, 1H), 2.97 (dd, J=4.2, 15.4 Hz, 1H), 3.62 (s, 3H), 3.90 (q, J=7.2 Hz, 2H), 4.18-4.25 (m, 1H), 6.63 (s, 1H), 7.34 (d, J=8.1 Hz, 1H), 7.55 (s, 1H).

Example 5

Production of N($\alpha$)-tert-butoxycarbonyl-N($\pi$)-propyl-L-histidine methyl ester N($\alpha$)-tert-butoxycarbonyl-N($\tau$)-triphenylmethyl-L-histidine methyl ester (48.6 g, 95 mmol) was dissolved in methylene chloride (400 mL) and propyl iodide (92 mL, 950 mmol) was added thereto followed by heating to reflux for 48 hours on an oil bath (temperature: 55° C.). Ethyl iodide (92 mL, 950 mmol) was further added thereto, the mixture was heated to reflux for 48 hours more and the solvent was evaporated in vacuo. Petroleum ether was added to the resulting oily residue, the mixture was subjected to a decantation for three times and dissolved in 80% acetic acid and then silver acetate (18.36 g, 110 mmol) was added thereto followed by stirring for 24 hours at room temperature. After the insoluble matters were filtered off, the solvent was evaporated in vacuo. The residue was dissolved in water and made alkaline by addition of anhydrous potassium carbonate and the oily product separated out therefrom was extracted with ethyl acetate. After it was dried over anhydrous sodium sulfate, the solvent was evaporated in vacuo. The oily residue was purified by a silica gel column chromatography (chloroform:methanol=19:1) to give N(α)-tert-butoxycarbonyl-N(π)-propyl-L-histidine methyl ester as an oily product.

$^1$H-NMR (DMSO-$d_6$) δ::0.84 (t, J=7.3 Hz, 3H), 1.36 (s, 9H), 1.62-1.72 (m, 2H), 2.87 (dd, J=9.8, 15.4 Hz, 1H), 2.97 (dd, J=4.2, 15.4 Hz, 1H), 3.62 (s, 3H), 3.78-3.88 (m, 2H), 4.18-4.25 (m, 1H), 6.64 (s, 1H), 7.36 (d, J=8.1 Hz, 1H), 7.53 (s, 1H).

Example 6

Production of N(α)-tert-butoxycarbonyl-N(π)-isopropyl-L-histidine methyl ester

N(α)-tert-butoxycarbonyl-N(τ)-triphenylmethyl-L-histidine methyl ester (48.6 g, 95 mmol) was dissolved in methylene chloride (400 mL) and isopropyl iodide (90 mL, 900 mmol) was added thereto followed by heating to reflux for 10 days on an oil bath (temperature: 55° C.). Petroleum ether was added to an oily residue prepared by evaporation of the solvent in vacuo, the mixture was subjected to a decantation for three times and dissolved in 80% acetic acid and then silver acetate (18.36 g, 110 mmol) was added thereto and stirred at room temperature for 24 hours. After the insoluble matters were filtered off, the solvent was evaporated in vacuo. The residue was dissolved in water and made alkaline by addition of anhydrous potassium carbonate and the oily product separated out therefrom was extracted with ethyl acetate. After it was dried over anhydrous sodium sulfate, the solvent was evaporated in vacuo. The oily residue was purified by a silica gel column chromatography (chloroform methanol=19:1) to give N(α)-tert-butoxycarbonyl-N(π)-isopropyl-L-histidine methyl ester as an oily product.

$^1$H-NMR (DMSO-$d_6$) δ: 1.35 (s, 9H), 1.37-1.42 (m, 6H), 2.87 (dd, J=9.8, 15.4 Hz, 1H), 2.97 (dd, J=4.2, 15.4 Hz, 1H), 3.62 (s, 3H), 4.18-4.29 (m, 2H), 6.61 (s, 1H), 7.34 (d, J=8.1 Hz, 1H), 7.68 (s, 1H).

Example 7

Production of N(α)-tert-butoxycarbonyl-N(π)-methyl-D-histidine methyl ester

In the same manner as in the synthesis of N(α)-tert-butoxycarbonyl-N(π)-methyl-L-histidine methyl ester, N(α)-tert-butoxycarbonyl-N(π)-methyl-D-histidine methyl ester was produced starting from D-histidine.

Mp. 107-109° C. $[α]_D^{20}$=☐12.4° (c1, MeOH). $^1$H-NMR (DMSO-$d_6$) δ: 1.35 (s, 9H), 2.87 (dd, J=9.8, 15.4 Hz, 1H), 2.97 (dd, J=4.2, 15.4 Hz, 1H), 3.53 (s, 3H), 3.62 (s, 3H), 4.18-4.25 (m, 1H), 6.64 (s, 1H), 7.33 (d, J=8.1 Hz, 1H), 7.48 (s, 1H).

Example 8

Production of N(α)-acryloyl-N(π)-methyl-L-histidine methyl ester

N(α)-tert-Butoxycarbonyl-N(π)-methyl-L-histidine methyl ester (11.33 g, 40 mmol) was dissolved in methylene chloride (150 mL) and a 4 mol/L hydrogen chloride/dioxane solution (100 mL) was dropped thereinto. After the mixture was stirred at room temperature for 2 hours, the solvent was evaporated in vacuo to give N(π)-methyl-L-histidine methyl ester. N(π)-Methyl-L-histidine methyl ester dihydrochloride was dissolved in methylene chloride (500 mL), then acrylic acid (4.1 mL, 60 mmol) and triethylamine (17 mL, 120 mmol) were added thereto and, after that, a solution of DCC (12.38 g, 60 mmol) in methylene chloride (50 mL) was dropped thereinto at room temperature. After stirring at room temperature for 20 hours, the insoluble matters were filtered off therefrom, the solvent of the filtrate was evaporated in vacuo and the residue was passed through a column filled with silica gel DM 1020 for chromatography of a type of binding to an aminopropyl group and eluted with chloroform. Fractions of the aimed product were collected, spread on a column filled with silica gel BW-127ZH for normal phase chromatography and eluted with chloroform:methanol (=19:1) to give N(α)-acryloyl-N(π)-methyl-L-histidine methyl ester (1.58 g, 17%) as an oily product.

$^1$H-NMR (DMSO-$d_6$) δ: 2.96 (dd, J=8.7, 15.4 Hz, 1H), 3.04 (dd, J=5.5, 15.4 Hz, 1H), 3.53 (s, 3H), 3.63 (s, 3H), 4.57-4.64 (m, 1H), 5.63 (dd, J=2.0, 10.3 Hz, 1H), 6.12 (dd, J=2.0, 16.9 Hz, 1H), 6.27 (dd, J=10.3, 16.9 Hz, 1H), 6.63 (s, 1H), 7.49 (s, 1H), 8.62 (d, J=7.8 Hz, 1H).

Example 9

Production of N(α)-acryloyl-N(π)-ethyl-L-histidine methyl ester

After N(π)-ethyl-L-histidine methyl ester was prepared from N(α)-tert-butoxycarbonyl-N(π)-ethyl-L-histidine methyl ester (7.43 g, 25 mmol), a 4 mol/L hydrogen chloride/dioxane solution (65 mL) and methylene chloride (65 mL), the same operation as in the synthesis of N(α)-acryloyl-N(π)-methyl-L-histidine methyl ester was conducted using acrylic acid (1.9 mL, 28 mmol), triethylamine (10 mL, 70 mmol), DCC (5.78 g, 28 mmol) and methylene chloride (300 mL) to give N(α)-acryloyl-N(π)-ethyl-L-histidine methyl ester (0.91 g, 14%) as an oily product.

$^1$H-NMR (DMSO-$d_6$) δ: 1.30 (t, J=7.4 Hz, 3H), (dd, J=8.7, 15.4 Hz, 1H), 3.04 (dd, J=5.5, 15.4 Hz, 1H), 3.63 (s, 3H), 3.90 (q, J=7.4 Hz, 2H), 4.57-4.64 (m, 1H), 5.63 (dd, J=2.0, 10.3 Hz, 1H), 6.12 (dd, J=2.0, 16.9 Hz, 1H), 6.27 (dd, J=10.3, 16.9 Hz, 1H), 6.63 (s, 1H), 7.56 (s, 1H), 8.62 (d, J=7.8 Hz, 1H).

Example 10

Production of N(α)-crotonoyl-N(π)-methyl-L-histidine methyl ester

After N(π)-methyl-L-histidine methyl ester was prepared from N(α)-tert-butoxycarbonyl-N(π)-methyl-L-histidine methyl ester (5.76 g, 20 mmol), a 4 mol/L hydrogen chloride/dioxane solution (50 mL) and methylene chloride (50 mL), the same operation as in the synthesis of N(α)-acryloyl-N(π)-methyl-L-histidine methyl ester was conducted using crotonic acid (2.58 mL, 30 mmol), triethylamine (8.4 mL, 60 mmol), DCC (6.19 g, 30 mmol) and methylene chloride (300 mL) to give N(α)-crotonoyl-N(π)-methyl-L-histidine methyl ester (3.04 g, 60%) as an oily product.

$^1$H-NMR (DMSO-$d_6$) δ: 1.79 (dd, J=1.5, 6.8 Hz, 3H), 2.96 (dd, J=8.7, 15.4 Hz, 1H), 3.04 (dd, J=5.5, 15.4 Hz, 1H), 3.53 (s, 3H), 3.62 (s, 3H), 4.54-4.61 (m, 1H), 5.95 (dd, J=1.5, 15.3 Hz, 1H), 6.59-6.68 (m, 1H), 6.64 (s, 1H), 7.48 (s, 1H), 8.38 (d, J=7.8 Hz, 1H).

Example 11

Production of N(α)-crotonoyl-N(π)-ethyl-L-histidine methyl ester

After N(π)-ethyl-L-histidine methyl ester was prepared from N(α)-tert-butoxycarbonyl-N(π)-ethyl-L-histidine methyl ester (4.00 g, 13.5 mmol), a 4 mol/L hydrogen chloride/dioxane solution (50 mL) and methylene chloride (50 mL), the same operation as in the synthesis of N(α)-acryloyl-N(π)-methyl-L-histidine methyl ester was conducted using crotonic acid (2.32 mL, 27 mmol), triethylamine (7.5 mL, 54 mmol), DCC (5.57 g, 27 mmol) and methylene chloride (300 mL) to give N(α)-crotonoyl-N(π)-ethyl-L-histidine methyl ester (1.11 g, 31%) as an oily product.

$^1$H-NMR (DMSO-$d_6$) δ: 1.29 (t, J=7.4 Hz, 3H), 1.79 (dd, J=1.5, 6.8 Hz, 3H), 2.96 (dd, J=8.7, 15.4 Hz, 1H), 3.04 (dd, J=5.5, 15.4 Hz, 1H), 3.62 (s, 3H), 3.89 (q, J=7.4 Hz, 2H), 4.54-4.61 (m, 1H), 5.95 (dd, J=1.5, 15.3 Hz, 1H), 6.59-6.68 (m, 1H), 6.64 (s, 1H), 7.55 (s, 1H), 8.39 (d, J=7.8 Hz, 1H).

Example 12

Production of N(α)-propanoyl-N(π)-methyl-L-histidine methyl ester

After N(π)-methyl-L-histidine methyl ester was prepared from N(α)-tert-butoxycarbonyl-N(π)-methyl-L-histidine methyl ester (4.25 g, 15 mmol), a 4 mol/L hydrogen chloride/dioxane solution (40 mL) and methylene chloride (40 mL), the same operation as in the synthesis of N(α)-acryloyl-N(π)-methyl-L-histidine methyl ester was conducted using propionic acid (1.7 mL, 22.5 mmol), triethylamine (7.0 mL, 50 mmol), DCC (4.64 g, 22.5 mmol) and methylene chloride (150 mL) to give N(α)-propanoyl-N(π)-methyl-L-histidine methyl ester (2.39 g, 67%) as an oily product.

$^1$H-NMR (DMSO-$d_6$) δ: 0.95 (t, J=7.3 Hz, 3H), 2.96 (dd, J=8.7, 15.4 Hz, 1H), 3.04 (dd, J=5.5, 15.4 Hz, 1H), 3.53 (s, 3H), 3.62 (s, 3H), 4.57-4.64 (m, 1H), 6.62 (s, 1H), 7.48 (s, 1H), 8.26 (d, J=7.8 Hz, 1H).

Example 13

Production of N(α)-3-methylcrotonoyl-N(π)-methyl-L-histidine methyl ester

After N(π)-methyl-L-histidine methyl ester was prepared from N(α)-tert-butoxycarbonyl-N(π)-methyl-L-histidine methyl ester (4.25 g, 15 mmol), a 4 mol/L hydrogen chloride/dioxane solution (40 mL) and methylene chloride (40 mL), the same operation as in the synthesis of N(α)-acryloyl-N(π)-methyl-L-histidine methyl ester was conducted using 3-methylcrotonic acid (3.0 g, 30 mmol), triethylamine (8.4 mL, 60 mmol), DCC (6.2 g, 30 mmol) and methylene chloride (200 mL) to give N(α)-3-methylcrotonoyl-N(π)-methyl-L-histidine methyl ester (2.00 g, 50%) as an oily product.

$^1$H-NMR (DMSO-$d_6$) δ: 1.78 (s, 3H), 2.04 (s, 3H), 2.96 (dd, J=8.7, 15.4 Hz, 1H), 3.04 (dd, J=5.5, 15.4 Hz, 1H), 3.53 (s, 3H), 3.62 (s, 3H), 4.57-4.64 (m, 1H), 5.69 (s, 1H), 6.63 (s, 1H), 7.48 (s, 1H), 8.21 (d, J=7.8 Hz, 1H).

Example 14

Production of N(π)-3-methylcrotonoyl-N(π)-ethyl-L-histidine methyl ester

After N(π)-ethyl-L-histidine methyl ester was prepared from N(α)-tert-butoxycarbonyl-N(π)-ethyl-L-histidine methyl ester (4.00 g, 13.5 mmol), a 4 mol/L hydrogen chloride/dioxane solution (40 mL) and methylene chloride (40 mL), the same operation as in the synthesis of N(α)-acryloyl-N(π)-methyl-L-histidine methyl ester was conducted using 3-methylcrotonic acid (2.30 g, 20 mmol), triethylamine (5.7 mL, 41 mmol), DCC (4.19 g, 20 mmol) and methylene chloride (150 mL) to give N(π)-3-methylcrotonoyl-N(π)-ethyl-L-histidine methyl ester (2.15 g, 57%) as an oily product.

$^1$H-NMR (DMSO-$d_6$) δ: 1.23 (t, J=7.3 Hz, 3H), 1.78 (s, 3H), 2.04 (s, 3H), 2.96 (dd, J=8.7, 15.4 Hz, 1H), 3.04 (dd, J=5.5, 15.4 Hz, 1H), 3.62 (s, 3H), 3.89 (q, J=7.3 Hz, 2H), 4.57-4.64 (m, 1H), 5.69 (s, 1H), 6.63 (s, 1H), 7.55 (s, 1H), 8.23 (d, J=7.8 Hz, 1H).

Example 15

Production of N(α)-3-phenylpropenoyl-N(π)-methyl-L-histidine methyl ester

After N(π)-methyl-L-histidine methyl ester was prepared from N(α)-tert-butoxycarbonyl-N(π)-methyl-L-histidine methyl ester (2.83 g, 10 mmol), a 4 mol/L hydrogen chloride/dioxane solution (30 mL) and methylene chloride (30 mL), the same operation as in the synthesis of N(α)-acryloyl-N(π)-methyl-L-histidine methyl ester was conducted using cinnamic acid (2.22 g, 15 mmol), triethylamine (4.2 mL, 30 mmol), DCC (3.11 g, 15 mmol) and methylene chloride (150 mL) to give N(α)-3-phenylpropenoyl-N(π)-methyl-L-histidine methyl ester (1.20 g, 38%) as an oily product.

$^1$H-NMR (DMSO-$d_6$) δ: 3.00 (dd, J=8.7, 15.4 Hz, 1H), 3.08 (dd, J=5.5, 15.4 Hz, 1H), 3.55 (s, 3H), 3.65 (s, 3H), 4.64-4.70 (m, 1H), 6.67 (s, 1H), 6.71 (d, J=15.8 Hz, 1H), 7.38-7.46 (m, 4H), 7.50 (s, 1H), 7.56-7.59 (m, 2H), 8.60 (d, J=7.8 Hz, 1H).

Example 16

Production of N(α)-3-phenylpropenoyl-N(π)-ethyl-L-histidine methyl ester

After N(π)-ethyl-L-histidine methyl ester was prepared from N(α)-tert-butoxycarbonyl-N(π)-methyl-L-histidine methyl ester (5.0 g, 17 mmol), a 4 mol/L hydrogen chloride/dioxane solution (30 mL) and methylene chloride (30 mL), the same operation as in the synthesis of N(α)-acryloyl-N(π)-methyl-L-histidine methyl ester was conducted using cinnamic acid (3.85 g, 26 mmol), triethylamine (7.2 mL, 52 mmol), DCC (5.36 g, 26 mmol) and methylene chloride (150 mL) to give N(α)-3-phenylpropenoyl-N(π)-ethyl-L-histidine methyl ester (1.00 g, 18%) as an oily product.

$^1$H-NMR (DMSO-$d_6$) δ: 1.30 (t, J=7.3 Hz, 3H), 3.00 (dd, J=8.7, 15.4 Hz, 1H), 3.08 (dd, J=5.5, 15.4 Hz, 1H), 3.65 (s, 3H), 3.91 (q, J=7.3 Hz, 2H), 4.64-4.70 (m, 1H), 6.67 (s, 1H), 6.68 (d, J=15.8 Hz, 1H), 7.38-7.46 (m, 4H), 7.50 (s, 1H), 7.56-7.59 (m, 2H), 8.60 (d, J=7.8 Hz, 1H).

Example 17

Production of N(α)-2-methyl-2-butenoyl-N(π)-methyl-L-histidine methyl ester

After N(π)-methyl-L-histidine methyl ester was prepared from N(α)-tert-butoxycarbonyl-N(π)-methyl-L-histidine methyl ester (2.83 g, 10 mmol), a 4 mol/L hydrogen chloride/dioxane solution (30 mL) and methylene chloride (30 mL), the same operation as in the synthesis of N(α)-acryloyl-N(π)-methyl-L-histidine methyl ester was conducted using trans-2,3-dimethylacrylic acid (1.50 g, 15 mmol), triethylamine (4.2 mL, 30 mmol), DCC (3.1 g, 15 mmol) and methylene chloride (150 mL) to give N(α)-2-methyl-2-butenoyl-N(π)-methyl-L-histidine methyl ester (1.45 g, 55%) as an oily product.

$^1$H-NMR (DMSO-$d_6$) δ: 1.67-1.71 (m, 6H), 3.01 (dd, J=8.7, 15.4 Hz, 1H), 3.05 (dd, J=5.5, 15.4 Hz, 1H), 3.52 (s, 3H), 3.62 (s, 3H), 4.48-4.54 (m, 1H), 6.28-6.35 (m, 1H), 6.63 (s, 1H), 7.47 (s, 1H), 8.12 (d, J=7.8 Hz, 1H).

Example 18

Production of N(α)-2-methyl-2-butenoyl-N(π)-ethyl-L-histidine methyl ester

After N(π)-methyl-L-histidine methyl ester was prepared from N(α)-tert-butoxycarbonyl-N(π)-ethyl-L-histidine methyl ester (4.0 g, 13.5 mmol), a 4 mol/L hydrogen chloride/dioxane solution (30 mL) and methylene chloride (30 mL), the same operation as in the synthesis of N(α)-acryloyl-N(π)-methyl-L-histidine methyl ester was conducted using trans-2,3-dimethylacrylic acid (1.50 g, 15 mmol), triethylamine (4.2 mL, 30 mmol), DCC (3.1 g, 15 mmol) and methylene chloride (150 mL) to give N(α)-2-methyl-2-butenoyl-N(π)-ethyl-L-histidine methyl ester (1.17 g, 31%) as an oily product.

$^1$H-NMR (DMSO-$d_6$) δ: 1.29 (t, J=7.4 Hz, 3H), 1.67-1.71 (m, 6H), 2.98-3.09 (m, 2H), 3.62 (s, 3H), 4.48-4.54 (m, 1H), 6.28-6.35 (m, 1H), 6.63 (s, 1H), 7.55 (s, 1H), 8.16 (d, J=7.8 Hz, 1H).

Example 19

Production of N(α)-acryloyl-N(π)-propyl-L-histidine methyl ester

After N(π)-propyl-L-histidine methyl ester was prepared from N(α)-tert-butoxycarbonyl-N(π)-propyl-L-histidine methyl ester (4.67 g, 15 mmol), a 4 mol/L hydrogen chloride/dioxane solution (50 mL) and methylene chloride (50 mL), the same operation as in the synthesis of N(α)-acryloyl-N(π)-methyl-L-histidine methyl ester was conducted using acrylic acid (1.6 g, 23 mmol), triethylamine (7.0 mL, 50 mmol), DCC (4.75 g, 23 mmol) and methylene chloride (150 mL) to give N(α)-acryloyl-N(π)-propyl-L-histidine methyl ester (0.37 g, 9%) as an oily product.

$^1$H-NMR (DMSO-$d_6$) δ: 0.84 (t, J=7.3 Hz, 3H), 1.61-1.71 (m, 2H), 2.96 (dd, J=8.7, 15.4 Hz, 1H), 3.04 (dd, J=5.5, 15.4 Hz, 1H), 3.63 (s, 3H), 3.78-3.88 (m, 2H), 4.57-4.64 (m, 1H), 5.63 (dd, J=2.0, 10.3 Hz, 1H), 6.12 (dd, J=2.0, 16.9 Hz, 1H), 6.27 (dd, J=10.3, 16.9 Hz, 1H), 6.63 (s, 1H), 7.54 (s, 1H), 8.63 (d, J=7.8 Hz, 1H).

Example 20

Production of N(α)-crotonoyl-N(π)-propyl-L-histidine methyl ester

After N(π)-propyl-L-histidine methyl ester was prepared from N(α)-tert-butoxycarbonyl-N(π)-propyl-L-histidine methyl ester (3.11 g, 10 mmol), a 4 mol/L hydrogen chloride/dioxane solution (30 mL) and methylene chloride (30 mL), the same operation as in the synthesis of N(α)-acryloyl-N(π)-methyl-L-histidine methyl ester was conducted using crotonic acid (1.29 g, 15 mmol), triethylamine (4.2 mL, 30 mmol), DCC (3.09 g, 15 mmol) and methylene chloride (150 mL) to give N(α)-crotonoyl-N(π)-propyl-L-histidine methyl ester (1.00 g, 36%) as an oily product.

$^1$H-NMR (DMSO-$d_6$) δ: 0.84 (t, J=7.3 Hz, 3H), 1.61-1.71 (m, 2H), 1.79 (dd, J=1.5, 6.8 Hz, 3H), 2.96 (dd, J=8.7, 15.4 Hz, 1H), 3.04 (dd, J=5.5, 15.4 Hz, 1H), 3.63 (s, 3H), 3.78-3.88 (m, 2H), 4.57-4.64 (m, 1H), 5.95 (dd, J=1.5, 15.3 Hz, 1H), 6.59-6.68 (m, 1H), 6.63 (s, 1H), 7.54 (s, 1H), 8.63 (d, J=7.8 Hz, 1H).

Example 21

Production of N(α)-acryloyl-N(π)-isopropyl-L-histidine methyl ester

After N(π)-isopropyl-L-histidine methyl ester was prepared from N(α)-tert-butoxycarbonyl-N(π)-isopropyl-L-histidine methyl ester (2.50 g, 8 mmol), a 4 mol/L hydrogen chloride/dioxane solution (40 mL) and methylene chloride (40 mL), the same operation as in the synthesis of N(α)-acryloyl-N(π)-methyl-L-histidine methyl ester was conducted using acrylic acid (0.82 g, 12 mmol), triethylamine (3.3 mL, 24 mmol), DCC (2.48 g, 12 mmol) and methylene chloride (100 mL) to give N(α)-acryloyl-N(π)-isopropyl-L-histidine methyl ester (0.19 g, 9%) as an oily product.

$^1$H-NMR (DMSO-$d_6$) δ: 1.35-1.42 (m, 6H), 2.96 (dd, J=8.7, 15.4 Hz, 1H), 3.07 (dd, J=5.5, 15.4 Hz, 1H), 3.63 (s, 3H), 4.22-4.30 (m, 1H), 4.57-4.62 (m, 1H), 5.63 (dd, J=2.0, 10.3 Hz, 1H), 6.10 (dd, J=2.0, 16.9 Hz, 1H), 6.27 (dd, J=10.3, 16.9 Hz, 1H), 6.60 (s, 1H), 7.69 (s, 1H), 8.62 (d, J=7.8 Hz, 1H).

Example 22

Production of N(α)-acryloyl-L-histidine methyl ester

After chloroacrylic acid (1.6 ml, 20 mmol) was dropped, with ice cooling, into a solution of histidine methyl ester dihydrochloride (6.05 g, 25 mmol) and triethylamine (14 mL, 100 mmol) in methylene chloride (200 mL), the same operation as in the synthesis of N(α)-acryloyl-N(π)-methyl-L-histidine methyl ester was conducted to give N(α)-acryloyl-L-histidine methyl ester (2.0 g, 36%) as an oily product.

$^1$H-NMR (DMSO-$d_6$) δ: 2.88 (dd, J=8.5, 14.6 Hz, 1H), 2.95 (dd, J=5.5, 14.6 Hz, 1H), 3.60 (s, 3H), 4.54-4.60 (m, 1H), 5.61 (dd, J=2.0, 10.1 Hz, 1H), 6.08 (dd, J=2.0, 17.0 Hz, 1H), 6.27 (dd, J=10.1, 17.0 Hz, 1H), 6.79 (s, 1H), 7.52 (s, 1H), 8.45 (d, J=7.5 Hz, 1H), 11.81 (brs, 1H).

Example 23

Production of N(α)-acryloyl-N(π)-methyl-D-histidine methyl ester

After a 4 mol/L hydrogen chloride/dioxane solution (50 mL) and methylene chloride (65 mL) were added to N(α)- tert-butoxycarbonyl-N(π)-methyl-D-histidine methyl ester (5.67 g, 20 mmol) whereby a Boc group was removed to give a hydrochloride, the same operation as in the synthesis of N(α)-acryloyl-N(π)-methyl-L-histidine methyl ester was conducted to give N(α)-acryloyl-N(π)-methyl-D-histidine methyl ester (0.70 g, 10%) as an oily product.

$^1$H-NMR (DMSO-$d_6$) δ: 2.96 (dd, J=8.7, 15.4 Hz, 1H), 3.04 (dd, J=5.5, 15.4 Hz, 1H), 3.53 (s, 3H), 3.63 (s, 3H), 4.57-4.64 (m, 1H), 5.63 (dd, J=2.0, 10.3 Hz, 1H), 6.12 (dd, J=2.0, 16.9 Hz, 1H), 6.27 (dd, J=10.3, 16.9 Hz, 1H), 6.63 (s, 1H), 7.49 (s, 1H), 8.62 (d, J=7.8 Hz, 1H).

Example 24

Production of N(α)-acryloyl-N(π)-methyl-L-histidine [Compound 1]

N(α)-Acryloyl-N(π)-methyl-L-histidine methyl ester (5.04 g, 21 mmol) was dissolved in methanol (125 mL) and a 1 mol/L aqueous solution of sodium hydroxide (25 mL, 25 mmol of NaOH) was added thereto at room temperature. After stirring for 30 minutes, the solvent was evaporated in vacuo. The residue was dissolved in water and benzenesulfonic acid beads of a polystyrene bonded type (9.0 g, corresponding to 26 mmol of benzenesulfonic acid) were added thereto. After confirming that the pH was 7, the beads were filtered off and the filtrate was filtered through a membrane filter of 0.45 μm. The filtrate was freeze-dried to give N(α)-acryloyl-N(π)-methyl-L-histidine (3.5 g, 75%) as a hygroscopic amorphous solid.

$[α]_D^{20}$=□42.0° (c1, $H_2O$). $^1$H NMR ($D_2O$) δ: 2.97 (dd, J=8.6, 15.7 Hz, 1H), 3.16 (dd, J=5.0, 15.7 Hz, 1H), 3.66 (s, 3H), 4.45 (dd, J=5.0, 8.6 Hz, 1H), 5.65 (d, J=10.4 Hz, 1H), 6.04 (dd, J=17.2 Hz, 1H), 6.17 (dd, J=10.4, 17.2 Hz, 1H), 6.96 (s, 1H), 8.11 (s, 1H).

Example 25

Production of N(α)-acryloyl-N(π)-ethyl-L-histidine [Compound 2]

N(α)-Acryloyl-N(π)-ethyl-L-histidine (0.67 g, 80%) was produced as a hygroscopic amorphous solid in the same manner as in the synthesis of the Compound 1 starting from N(α)-acryloyl-N(π)-ethyl-L-histidine methyl ester (0.88 g, 3.5 mmol), methanol (40 mL), a 1 mol/L aqueous solution of sodium hydroxide (4.0 mL, 4.0 mmol of NaOH) and benzenesulfonic acid beads of a polystyrene bonding type (1.7 g, corresponding to 5.0 mmol of benzenesulfonic acid).

$^1$H NMR ($D_2O$) δ: 1.38 (t, J=7.3 Hz, 3H), 3.01 (dd, J=8.7, 15.8 Hz, 1H), 3.20 (dd, J=4.9, 15.8 Hz, 1H), 4.05 (q, J=7.3 Hz, 2H), 4.48 (dd, J=4.9, 8.7 Hz, 1H), 5.67 (d, J=15.4 Hz, 1H), 6.07 (d, J=17.3 Hz, 1H), 6.20 (dd, J=15.4, 17.3 Hz, 1H), 7.00 (s, 1H), 8.23 (s, 1H).

Example 26

Production of N(α)-crotonoyl-N(π)-methyl-L-histidine [Compound 3]

N(α)-Crotonoyl-N(π)-methyl-L-histidine (1.55 g, 65%) was produced as a hygroscopic amorphous solid in the same manner as in the synthesis of the Compound 1 starting from N(α)-crotonoyl-N(π)-methyl-L-histidine methyl ester (2.51 g, 10 mmol), methanol (100 mL), a 1 mol/L aqueous solution of sodium hydroxide (12 mL, 12 mmol of NaOH) and benzenesulfonic acid beads of a polystyrene bonding type (3.5 g, corresponding to 10.2 mmol of benzenesulfonic acid).

$^1$H NMR ($D_2O$) δ: 1.76 (dd, J=1.6, 7.0 Hz, 3H), 2.96 (dd, J=8.5, 15.6 Hz, 1H), 3.14 (dd, J=5.0, 15.6 Hz, 1H), 3.63 (s, 3H), 4.45 (dd, J=5.0, 8.5 Hz, 1H), 5.90 (dd, J=1.6, 15.7 Hz, 1H), 6.62-6.72 (m, 1H), 6.68 (s, 1H), 7.93 (s, 1H).

Example 27

Production of N(α)-crotonoyl-N(π)-ethyl-L-histidine [Compound 4]

N(α)-Crotonoyl-N(π)-ethyl-L-histidine (0.60 g, 57%) was produced as a hygroscopic amorphous solid in the same manner as in the synthesis of the Compound 1 starting from N(α)-crotonoyl-N(π)-ethyl-L-histidine methyl ester (1.11 g, 4.2 mmol), methanol (30 mL), a 1 mol/L aqueous solution of sodium hydroxide (5 mL, 5 mmol of NaOH) and benzenesulfonic acid beads of a polystyrene bonding type (1.5 g, corresponding to 4.5 mmol of benzenesulfonic acid).

$^1$H NMR ($D_2O$) δ 1.38 (t, J=7.3 Hz, 3H), 1.76 (d, J=6.9 Hz, 3H), 3.00 (dd, J=8.5, 15.6 Hz, 1H), 3.19 (dd, J=5.0, 15.6 Hz, 1H), 4.02 (q, J=7.3 Hz, 2H), 4.06 (dd, J=5.0, 8.5 Hz, 1H), 5.90 (d, J=16.7 Hz, 1H), 6.61-6.71 (m, 1H), 6.99 (s, 1H), 8.26 (s, 1H).

Example 28

Production of N(α)-3-methylcrotonoyl-N(π)-methyl-L-histidine [Compound 5]

N(α)-3-Methylcrotonoyl-N(π)-methyl-L-histidine (0.91 g, 48%) was produced as a hygroscopic amorphous solid in the same manner as in the synthesis of the Compound 1 starting from N(α)-3-methylcrotonoyl-N(π)-methyl-L-histidine methyl ester (2.00 g, 7.5 mmol), methanol (80 mL), a 1 mol/L aqueous solution of sodium hydroxide (9 mL, 9 mmol of NaOH) and benzenesulfonic acid beads of a polystyrene bonding type (4.0 g, corresponding to 12 mmol of benzenesulfonic acid).

$^1$H NMR ($D_2O$) δ 1.74 (s, 3H), 1.84 (s, 3H), 2.94 (dd, J=8.6, 15.7 Hz, 1H), 3.16 (dd, J=4.9, 15.7 Hz, 1H), 3.70 (s, 3H), 4.04 (dd, J=4.9, 8.6 Hz, 1H), 5.64 (s, 1H), 7.04 (s, 1H), 8.29 (s, 1H).

Example 29

Production of N(π)-3-phenylpropenoyl-N(π)-methyl-L-histidine [Compound 6]

N(π)-3-Phenylpropenoyl-N(π)-methyl-L-histidine (0.67 g, 59%) was produced as a hygroscopic amorphous solid in the same manner as in the synthesis of the Compound 1 starting from N(α)-3-phenylpropenoyl-N(π)-methyl-L-histidine methyl ester (1.20 g, 3.8 mmol), methanol (50 mL), a 1 mol/L aqueous solution of sodium hydroxide (8 mL, 8 mmol of NaOH) and benzenesulfonic acid beads of a polystyrene bonding type (3.0 g, corresponding to 9 mmol of benzenesulfonic acid).

$^1$H NMR ($D_2O$) δ 3.03 (dd, J=8.3, 15.8 Hz, 1H), 3.22 (dd, J=5.1, 15.8 Hz, 1H), 3.72 (s, 3H), 4.54 (dd, J=5.1, 8.3 Hz,

1H), 6.59 (d, J=15.8 Hz, 1H), 7.06 (s, 1H), 7.35-7.39 (m, 4H), 7.52-7.56 (m, 2H), 8.28 (s, 1H).

Example 30

Production of N(α)-2-methyl-2-butenoyl-N(π)-methyl-L-histidine [Compound 7]

N(α)-2-Methyl-3-butenoyl-N(π)-methyl-L-histidine (0.94 g, 75%) was produced as a hygroscopic amorphous solid in the same manner as in the synthesis of the Compound 1 starting from N(α)-2-methyl-3-butenoyl-N(π)-methyl-L-histidine methyl ester (1.33 g, 5.0 mmol), methanol (50 mL), a 1 mol/L aqueous solution of sodium hydroxide (8 mL, 8 mmol of NaOH) and benzenesulfonic acid beads of a polystyrene bonding type (3.0 g, corresponding to 9 mmol of benzenesulfonic acid).

$^1$H NMR (D$_2$O) δ 1.63 (d, J=7.8 Hz, 3H), 1.67 (s, 3H), 3.00 (dd, J=8.3, 15.8 Hz, 1H), 3.19 (dd, J=5.0, 15.8 Hz, 1H), 3.70 (s, 3H), 4.44 (dd, J=5.0, 8.3 Hz, 1H), 6.24-6.30 (m, 1H), 7.04 (s, 1H), 8.31 (s, 1H).

Example 31

Production of N(α)-acryoyl-N(π)-propyl-L-histidine [Compound 8]

N(π)-2-Acryloyl-N(π)-propyl-L-histidine (0.19 g, 53%) was produced as a hygroscopic amorphous solid in the same manner as in the synthesis of the Compound 1 starting from N(α)-acryloyl-N(π)-propyl-L-histidine methyl ester (0.37 g, 1.4 mmol), methanol (20 mL), a 1 mol/L aqueous solution of sodium hydroxide (2 mL, 2 mmol of NaOH) and benzenesulfonic acid beads of a polystyrene bonding type (0.75 g, corresponding to 2.3 mmol of benzenesulfonic acid).

$^1$H NMR (D$_2$O) δ: 0.82 (t, J=7.4 Hz, 3H), 1.72-7.79 (m, 2H), 3.01 (dd, J=8.3, 15.8 Hz, 1H), 3.21 (dd, J=5.0, 15.8 Hz, 1H), 3.94-4.04 (m, 2H), 4.49 (dd, J=5.0, 8.3 Hz, 1H), 5.67 (d, J=10.3 Hz, 1H), 6.06 (d, J=17.0 Hz, 1H), 6.20 (dd, J=10.3, 17.0 Hz, 1H), 7.07 (s, 1H), 8.39 (s, 1H).

Example 32

Production of N(α)-3-methylcrotonoyl-N(π)-ethyl-L-histidine [Compound 9]

N(α)-3-Methylcrotonoyl-N(π)-ethyl-L-histidine (0.91 g, 45%) was produced as a hygroscopic amorphous solid in the same manner as in the synthesis of the Compound 1 starting from N(α)-3-methylcrotonoyl-N(π)-ethyl-L-histidine methyl ester (2.2 g, 7.7 mmol), methanol (80 mL), a 1 mol/L aqueous solution of sodium hydroxide (10 mL, 7.7 mmol of NaOH) and benzenesulfonic acid beads of a polystyrene bonding type (4.0 g, corresponding to 12 mmol of benzenesulfonic acid).

$^1$H NMR (D$_2$O) δ: 1.40 (t, J=7.4 Hz, 3H), 1.72 (s, 3H), 1.84 (s, 3H), 2.98 (dd, J=8.6, 15.8 Hz, 1H), 3.18 (dd, J=5.0, 15.8 Hz, 1H), 4.07 (q, J=7.4 Hz, 2H), 4.44 (dd, J=5.0, 8.6 Hz, 1H), 5.45 (s, 1H), 7.09 (s, 1H), 8.48 (s, 1H).

Example 33

Production of N(α)-3-phenylpropenoyl-N(π)-ethyl-L-histidine [Compound 10]

N(α)-3-Phenylpropenoyl-N(π)-ethyl-L-histidine (0.36 g, 38%) was produced as a hygroscopic amorphous solid in the same manner as in the synthesis of the Compound 1 starting from N(α)-3-phenylpropenoyl-N(π)-ethyl-L-histidine methyl ester (0.98 g, 3.0 mmol), methanol (50 mL), a 1 mol/L aqueous solution of sodium hydroxide (5 mL, 5 mmol of NaOH) and benzenesulfonic acid beads of a polystyrene bonding type (2.0 g, corresponding to 6 mmol of benzenesulfonic acid).

$^1$H NMR (D$_2$O) δ 1.36 (t, J=7.4 Hz, 3H), 3.02 (dd, J=8.3, 15.8 Hz, 1H), 3.21 (dd, J=5.1, 15.8 Hz, 1H), 4.04 (q, J=7.4 Hz, 2H), 4.52 (dd, J=5.1, 8.3 Hz, 1H), 6.56 (d, J=15.8 Hz, 1H), 7.00 (s, 1H), 7.32-7.38 (m, 4H), 7.48-7.54 (m, 2H), 8.25 (s, 1H).

Example 34

Production of N(α)-2-methyl-2-butenoyl-N(π)-ethyl-L-histidine [Compound 11]

N(α)-2-Methyl-2-butenoyl-N(π)-ethyl-L-histidine (0.67 g, 60%) was produced as a hygroscopic amorphous solid in the same manner as in the synthesis of the Compound 1 starting from N(α)-2-methyl-2-butenoyl-N(π)-ethyl-L-histidine methyl ester (1.17 g, 4.2 mmol), methanol (50 mL), a 1 mol/L aqueous solution of sodium hydroxide (6 mL, 6 mmol of NaOH) and benzenesulfonic acid beads of a polystyrene bonding type (2.5 g, corresponding to 7.5 mmol of benzenesulfonic acid).

$^1$H NMR (D$_2$O) δ 1.40 (t, J=7.4 Hz, 3H), 1.65 (d, J=6.7 Hz, 3H), 1.81 (s, 3H), 3.02 (dd, J=8.3, 15.8 Hz, 1H), 3.23 (dd, J=5.1, 15.8 Hz, 1H), 4.09 (q, J=7.4 Hz, 2H), 4.46 (dd, J=5.1, 8.3 Hz, 1H), 6.25-6.30 (m, 1H), 7.08 (s, 1H), 8.46 (s, 1H).

Example 35

Production of N(α)-crotonoyl-N(π)-propyl-L-histidine [Compound 12]

N(α)-2-Crotonoyl-N(π)-propyl-L-histidine (0.59 g, 62%) was produced as a hygroscopic amorphous solid in the same manner as in the synthesis of the Compound 1 starting from N(α)-crotonoyl-N(π)-propyl-L-histidine methyl ester (1.00 g, 3.6 mmol), methanol (50 mL), a 1 mol/L aqueous solution of sodium hydroxide (6 mL, 6 mmol of NaOH) and benzenesulfonic acid beads of a polystyrene bonding type (2.0 g, corresponding to 2.9 mmol of benzenesulfonic acid).

$^1$H NMR (D$_2$O) δ: 0.81 (t, J=7.4 Hz, 3H), 1.72-1.80 (m, 5H), 3.00 (dd, J=8.3, 15.8 Hz, 1H), 3.18 (dd, J=4.9, 15.8 Hz, 1H), 3.96-4.04 (m, 2H), 4.46 (dd, J=4.9, 8.3 Hz, 1H), 5.90 (dd, J=1.7, 15.4 Hz, 1H), 6.63-6.72 (m, 1H), 7.04 (s, 1H), 8.35 (s, 1H).

Example 36

Production of N(α)-acryloyl-N(π)-isopropyl-L-histidine [Compound 13]

N(α)-2-Acryloyl-N(π)-isopropyl-L-histidine (0.05 g, 28%) was produced as a hygroscopic amorphous solid in the same manner as in the synthesis of the Compound 1 starting from N(α)-acryloyl-N(π)-isopropyl-L-histidine methyl ester (0.19 g, 0.7 mmol), methanol (30 mL), a 1 mol/L aqueous solution of sodium hydroxide (2.2 mL, 2.2 mmol of NaOH) and benzenesulfonic acid beads of a polystyrene bonding type (1.0 g, corresponding to 3.0 mmol of benzenesulfonic acid).

¹H NMR (D₂O) δ: 1.45 (d, J=6.7 Hz, 3H), 1.48 (d, J=6.7 Hz, 3H), 3.06 (dd, J=8.3, 15.8 Hz, 1H), 3.29 (dd, J=5.0, 15.8 Hz, 1H), 4.52 (dd, J=5.0, 8.3 Hz, 1H), 4.55-4.60 (m, 1H), 5.70 (d, J=10.4, 1H), 6.09 (d, J=17.1 Hz, 1H), 6.22 (dd, J=10.4, 17.1 Hz, 1H), 7.13 (s, 1H), 8.62 (s, 1H).

Example 37

Production of N(α)-acryloyl-L-histidine [Compound 14]

N(α)-2-Acryloyl-L-histidine (0.59 g, 31%) was produced as a hygroscopic amorphous solid in the same manner as in the synthesis of the Compound 1 starting from N(α)-acryloyl-L-histidine methyl ester (2.00 g, 9.0 mmol), methanol (60 mL), a 1 mol/L aqueous solution of sodium hydroxide (15 mL, 15 mmol of NaOH) and benzenesulfonic acid beads of a polystyrene bonding type (6.0 g, corresponding to 18 mmol of benzenesulfonic acid).

¹H NMR (D₂O) δ 3.02 (dd, J=8.3, 15.8 Hz, 1H), 3.21 (dd, J=5.1, 15.8 Hz, 1H), 4.49 (dd, J=5.1, 8.3 Hz, 1H), 5.66 (d, J=10.4 Hz, 1H), 6.06 (d, J=17.0 Hz, 1H), 6.18 (dd, J=10.4, 17.0, 1H), 7.14 (s, 1H), 8.45 (s, 1H).

Example 38

Production of N(α)-acryloyl-N(π)-methyl-D-histidine [Compound 15]

N(α)-Acryloyl-N(π)-methyl-D-histidine (0.25 g, 37%) was produced as a hygroscopic amorphous solid in the same manner as in the synthesis of the Compound 1 starting from N(α)-acryloyl-N(π)-methyl-D-histidine methyl ester (0.7 g, 3.0 mmol), methanol (40 mL), a 1 mol/L aqueous solution of sodium hydroxide (5 mL, 5 mmol of NaOH) and benzenesulfonic acid beads of a polystyrene bonding type (2.0 g, corresponding to 6 mmol of benzenesulfonic acid).

[α]$_D^{20}$=−38.0° (c1, H₂O). ¹H NMR (D₂O) δ 3.01 (dd, J=8.6, 15.7 Hz, 1H), 3.21 (dd, J=5.0, 15.7 Hz, 1H), 3.74 (s, 3H), 4.45 (dd, J=5.0, 8.6 Hz, 1H), 5.66 (d, J=10.4 Hz, 1H), 6.06 (dd, J=17.2 Hz, 1H), 6.18 (dd, J=10.4, 17.2 Hz, 1H), 7.11 (s, 1H), 8.45 (s, 1H).

Example 39

Production of N(α)-3-(4-methylphenyl)acryloyl-N(π)-methyl-L-histidine methyl ester N(π)-Methyl-L-histidine methyl ester trihydrochloride (7.0 g, 24 mmol) was dissolved in methylene chloride (400 mL), triethylamine (20 mL, 44 mmol) was added thereto and, after that, a solution of 4-methylcinnamoyl chloride (5.1 g, 28 mmol) in methylene chloride (50 mL) was dropped thereinto under ice cooling. After the mixture was stirred at room temperature for 5 hours, it was washed with water and with a saturated saline solution and the organic layer was dried over anhydrous sodium sulfate. The solvent was evaporated in vacuo and the resulting oily residue was purified by a silica gel column chromatography (chloroform:methanol=19:1) to give N(α)-3-(4-methylphenyl)acryloyl-N(π)-methyl-L-histidine methyl ester (4.8 g, 61%) as an oily product.

¹H-NMR (DMSO-d₆) δ 2.32 (s, 3H), 3.00 (dd, J=8.5, 15.5 Hz, 1H), 3.09 (dd, J=5.5, 15.5 Hz, 1H), 3.55 (s, 3H), 3.66 (s, 3H), 4.68 (m, 1H), 6.66 (d, J=15.9 Hz, 1H), 6.68 (s, 1H), 7.22 (d, J=8.0 Hz, 2H), 7.41 (d, J=15.9 Hz, 1H), 7.46 (d, J=8.0 Hz, 2H), 7.51 (s, 1H), 8.58 (d, J=5.8 Hz, 1H).

Example 40

Production of N(α)-3-(4-methoxyphenyl)acryloyl-N(π)-methyl-L-histidine methyl ester N(α)-3-(4-Methoxyphenyl)acryloyl-N(π)-methyl-L-histidine methyl ester (3.3 g, 40%) was prepared as an oily substance by the same manner as in the production of N(α)-3-(4-methylphenyl)acryloyl-N(π)-methyl-L-histidine methyl ester starting from N(π)-methyl-L-histidine methyl ester trihydrochloride (7.0 g, 24 mmol), triethylamine (20 mL, 44 mmol), 4-methoxycinnamoyl chloride (5.5 g, 28 mmol) and methylene chloride (450 mL).

¹H-NMR (DMSO-d₆) δ 2.99 (dd, J=8.7, 15.6 Hz, 1H), 3.08 (dd, J=5.5, 15.6 Hz, 1H), 3.55 (s, 3H), 3.65 (s, 3H), 3.79 (s, 3H), 4.67 (m, 1H), 6.56 (d, J=15.7 Hz, 1H), 6.67 (s, 1H), 6.98 (d, J=8.7 Hz, 2H), 7.39 (d, J=15.7 Hz, 1H), 7.50 (s, 1H), 7.52 (d, J=8.7 Hz, 2H), 8.51 (d, J=7.9 Hz, 1H).

Example 41

Production of N(α)-3-(4-chlorophenyl)acryloyl-N(π)-methyl-L-histidine methyl ester N(α)-3-(4-Methoxyphenyl)acryloyl-N(π)-methyl-L-histidine methyl ester (7.1 g, 86%) was prepared as an oily substance by the same manner as in the production of N(α)-3-(4-methylphenyl)acryloyl-N(π)-methyl-L-histidine methyl ester starting from N(π)-methyl-L-histidine methyl ester trihydrochloride (7.0 g, 24 mmol), triethylamine (20 mL, 44 mmol), 4-chlorocinnamoyl chloride (5.6 g, 28 mmol) and methylene chloride (450 mL).

¹H-NMR (DMSO-d₆) δ 3.00 (dd, J=8.7, 15.5 Hz, 1H), 3.09 (dd, J=5.5, 15.5 Hz, 1H), 3.55 (s, 3H), 3.66 (s, 3H), 4.68 (m, 1H), 6.67 (s, 1H), 6.72 (d, J=15.8 Hz, 1H), 7.44 (d, J=15.8 Hz, 1H), 7.48 (d, J=8.6 Hz, 2H), 7.50 (s, 1H), 7.60 (d, J=8.6 Hz, 2H), 8.63 (d, J=7.8 Hz, 1H).

Example 42

Production of N(α)-3-(3,4-dichlorophenyl)acryloyl-N(π)-methyl-L-histidine methyl ester N(α)-3-(3,4-Dichlorophenyl)acryloyl-N(π)-methyl-L-histidine methyl ester (7.5 g, 65%) was prepared as an oily substance by the same manner as in the production of N(α)-3-(4-methylphenyl)acryloyl-N(π)-methyl-L-histidine methyl ester starting from N(π)-methyl-L-histidine methyl ester trihydrochloride (7.0 g, 24 mmol), triethylamine (20 mL, 44 mmol), 3,4-dichlorocinnamoyl chloride (8.2 g, 28 mmol) and methylene chloride (450 mL).

¹H-NMR (DMSO-d₆) δ 3.01 (dd, J=8.5, 15.5 Hz, 1H), 3.09 (dd, J=5.5, 15.5 Hz, 1H), 3.55 (s, 3H), 3.66 (s, 3H), 4.68 (m, 1H), 6.67 (s, 1H), 6.78 (d, J=15.9 Hz, 1H), 7.43 (d, J=15.9 Hz, 1H), 7.51 (s, 1H), 7.57 (m, 1H), 7.68 (d, J=8.6 Hz, 1H), 7.86 (s, 1H), 8.63 (d, J=7.8 Hz, 1H).

Example 43

Production of N(α)-3-(4-fluorophenyl)acryloyl-N(π)-methyl-L-histidine methyl ester N(α)-3-(4-Fluorophenyl)acryloyl-N(π)-methyl-L-histidine methyl ester (7.7 g, 96%) was prepared as an oily substance by the same manner as in the production of N(α)-3-(4-methylphenyl)acryloyl-N(π)-methyl-L-histidine methyl ester starting from N(π)-methyl-L-histidine methyl ester trihydrochloride (7.0 g, 24 mmol), triethylamine (20 mL, 44 mmol), 4-fluorocinnamoyl chloride (5.2 g, 28 mmol) and methylene chloride (450 mL).

$^1$H-NMR (DMSO-$d_6$) δ 3.00 (dd, J=8.6, 15.5 Hz, 1H), 3.08 (dd, J=5.5, 15.5 Hz, 1H), 3.55 (s, 3H), 3.65 (s, 3H), 4.67 (m, 1H), 6.65 (m, 1H), 6.67 (s, 1H), 7.26 (m, 2H), 7.44 (m, 1H), 7.50 (s, 1H), 7.63 (m, 2H), 8.60 (d, J=7.8 Hz, 1H).

Example 44

Production of N(α)-3-(3,5-bistrifluoromethylphenyl)-acryloyl-N(π)-methyl-L-histidine methyl ester N(α)-3-(3,5-Bistrifluoromethylphenyl)acryloyl-N(π)-methyl-L-histidine methyl ester (9.2 g, 85%) was prepared as an oily substance by the same manner as in the production of N(α)-3-(4-methylphenyl)acryloyl-N(π)-methyl-L-histidine methyl ester starting from N(π)-methyl-L-histidine methyl ester trihydrochloride (7.0 g, 24 mmol), triethylamine (20 mL, 44 mmol), 3,5-bistrifluoromethylcinnamoyl chloride (8.5 g, 28 mmol) and methylene chloride (450 mL).

$^1$H-NMR (DMSO-$d_6$) δ 3.02 (dd, J=8.6, 15.6 Hz, 1H), 3.10 (dd, J=5.4, 15.6 Hz, 1H), 3.55 (s, 3H), 3.67 (s, 3H), 4.70 (m, 1H), 6.68 (s, 1H), 7.02 (d, J=16.0 Hz, 1H), 7.51 (s, 1H), 7.63 (d, J=16.0 Hz, 1H), 8.10 (s, 1H), 8.29 (s, 2H), 8.61 (d, J=7.8 Hz, 1H).

Example 45

Production of N(α)-3-(4-isobutylphenyl)acryloyl-N(π)-methyl-L-histidine methyl ester N(α)-3-(4-Isobutylphenyl)acryloyl-N(π)-methyl-L-histidine methyl ester (7.0 g, 78%) was prepared as an oily substance by the same manner as in the production of N(α)-3-(4-methylphenyl)acryloyl-N(π)-methyl-L-histidine methyl ester starting from N(π)-methyl-L-histidine methyl ester trihydrochloride (7.0 g, 24 mmol), triethylamine (20 mL, 44 mmol), 4-isobutylcinnamoyl chloride (6.2 g, 28 mmol) and methylene chloride (450 mL).

$^1$H-NMR (DMSO-$d_6$) δ 0.86 (d, J=6.6 Hz, 6H), 1.84 (m, 1H), 2.47 (d, J=7.1 Hz, 2H), 3.00 (dd, J=8.5, 15.5 Hz, 1H), 3.08 (dd, J=5.5, 15.5 Hz, 1H), 3.55 (s, 3H), 3.65 (s, 3H), 4.67 (m, 1H), 6.65 (d, J=15.8 Hz, 1H), 6.66 (s, 1H), 7.21 (d, J=7.9 Hz, 2H), 7.41 (d, J=15.8 Hz, 1H), 7.48 (d, J=7.9 Hz, 2H), 7.50 (s, 1H), 8.57 (d, J=7.8 Hz, 1H).

Example 46

Production of N(α)-3-(3,4-dimethoxyphenyl)acryloyl-N(π)-methyl-L-histidine methyl ester N(α)-3-(3,4-Dimethoxyphenyl)acryloyl-N(π)-methyl-L-histidine methyl ester (4.9 g, 54%) was prepared as an oily substance by the same manner as in the production of N(α)-3-(4-methylphenyl)acryloyl-N(π)-methyl-L-histidine methyl ester starting from N(π)-methyl-L-histidine methyl ester trihydrochloride (7.0 g, 24 mmol), triethylamine (20 mL, 44 mmol), 3,4-dimethoxycinnamoyl chloride (6.3 g, 28 mmol) and methylene chloride (450 mL).

$^1$H-NMR (DMSO-$d_6$) δ 3.00 (dd, J=8.7, 15.5 Hz, 1H), 3.08 (dd, J=5.5, 15.5 Hz, 1H), 3.56 (s, 3H), 3.66 (s, 3H), 3.79 (s, 3H), 3.81 (s, 3H), 4.67 (m, 1H), 6.60 (d, J=15.7 Hz, 1H), 6.67 (s, 1H), 6.98 (m, 1H), 7.12 (m, 1H), 7.16 (s, 1H), 7.38 (d, J=15.7 Hz, 1H), 8.48 (d, J=7.8 Hz, 1H).

Example 47

Production of N(α)-3-(4-nitrophenyl)acryloyl-N(π)-methyl-L-histidine methyl ester N(α)-3-(4-Nitrophenyl)acryloyl-N(π)-methyl-L-histidine methyl ester (8.5 g, 98%) was prepared as an oily substance by the same manner as in the production of N(α)-3-(4-methylphenyl)acryloyl-N(π)-methyl-L-histidine methyl ester starting from N(π)-methyl-L-histidine methyl ester trihydrochloride (7.0 g, 24 mmol), triethylamine (20 mL, 44 mmol), 4-nitrocinnamoyl chloride (5.9 g, 28 mmol) and methylene chloride (450 mL).

$^1$H-NMR (DMSO-$d_6$) δ 3.01 (dd, J=8.6, 15.5 Hz, 1H), 3.10 (dd, J=5.5, 15.5 Hz, 1H), 3.56 (s, 3H), 3.66 (s, 3H), 4.69 (m, 1H), 6.67 (s, 1H), 6.90 (d, J=15.7 Hz, 1H), 7.51 (s, 1H), 7.56 (d, J=15.7 Hz, 1H), 7.84 (d, J=8.7 Hz, 2H), 8.26 (d, J=8.7 Hz, 2H), 8.77 (d, J=7.8 Hz, 1H).

Example 48

Production of N(α)-3-(3-cyanophenyl)acryloyl-N(π)-methyl-L-histidine methyl ester N(α)-3-(3-Cyanophenyl)acryloyl-N(π)-methyl-L-histidine methyl ester (5.7 g, 70%) was prepared as an oily substance by the same manner as in the production of N(α)-3-(4-methylphenyl)acryloyl-N(π)-methyl-L-histidine methyl ester starting from N(π)-methyl-L-histidine methyl ester trihydrochloride (7.0 g, 24 mmol), triethylamine (20 mL, 44 mmol), 3-cyanocinnamoyl chloride (5.4 g, 28 mmol) and methylene chloride (450 mL).

$^1$H-NMR (DMSO-$d_6$) δ 3.00 (dd, J=8.7, 15.6 Hz, 1H), 3.09 (dd, J=5.5, 15.6 Hz, 1H), 3.55 (s, 3H), 3.66 (s, 3H), 4.67 (m, 1H), 6.67 (s, 1H), 6.82 (d, J=15.8 Hz, 1H), 7.48 (d, J=15.8 Hz, 1H), 7.50 (s, 1H), 7.63 (t, J=7.8, 7.8 Hz, 1H), 7.84 (d, J=7.8 Hz, 1H), 7.91 (d, J=7.8 Hz, 1H), 8.05 (s, 1H), 8.65 (d, J=7.8 Hz, 1H).

Example 49

Production of N(α)-3-(3-methoxyphenyl)acryloyl-N(π)-methyl-L-histidine methyl ester N(α)-3-(3-Methoxyphenyl)acryloyl-N(π)-methyl-L-histidine methyl ester (7.9 g, 95%) was prepared as an oily substance by the same manner as in the production of N(α)-3-(4-methylphenyl)acryloyl-N(π)-methyl-L-histidine methyl ester starting from N(π)-methyl-L-histidine methyl ester trihydrochloride (7.0 g, 24 mmol), triethylamine (20 mL, 44 mmol), 3-methoxycinnamoyl chloride (5.5 g, 28 mmol) and methylene chloride (450 mL).

$^1$H-NMR (DMSO-$d_6$) δ 3.01 (dd, J=8.7, 15.5 Hz, 1H), 3.09 (dd, J=5.5, 15.5 Hz, 1H), 3.56 (s, 1H), 3.66 (s, 1H), 3.79 (s, 1H), 4.69 (m, 1H), 6.67 (s, 1H), 6.72 (d, J=15.7 Hz, 1H), 6.97 (m, 1H), 7.14 (m, 2H), 7.34 (m, 1H), 7.42 (d, J=15.7 Hz, 1H), 7.51 (s, 1H), 8.59 (d, J=7.8 Hz, 1H).

Example 50

Production of N(α)-3-(4-methylphenyl)acryloyl-N(π)-methyl-L-histidine [Compound 16]

N(α)-3-(4-Methylphenyl)acryloyl-N(π)-methyl-L-histidine methyl ester (4.5 g, 14 mmol) was dissolved in methanol (300 mL), a 1 mol/L aqueous solution of sodium hydroxide (21 mL, 21 mmol of NaOH) was added thereto at room temperature and the mixture was stirred for 3 hours. The solvent was evaporated in vacuo, the resulting residue was dissolved in water (100 mL) and p-toluenesulfonic acid beads of a polystyrene-bonding type (8.9 g, corresponding to 21 mmol of p-toluenesulfonic acid) were added thereto. After confirming that the pH was 7, the beads were filtered off using a membrane filter of 0.45 μm. When the filtrate was evaporated in vacuo, crystals were isolated therefrom. The crystals were dried, ether was added thereto and the mixture was filtered followed by drying on phosphorus pentaoxide in vacuo at room temperature for 48 hours to give N(α)-3-(4-methylphenyl)acryloyl-N(π)-methyl-L-histidine (2.6 g, 59%).

Mp. 58-59. $[α]_D^{20}$=+10.3° (c1, 0.1 mol/L NaOH). $^1$H-NMR DMSO-$d_6$ δ 2.31 (s, 3H), 2.93 (dd, J=7.3, 15.3 Hz, 1H), 3.08 (dd, J=5.0, 15.3 Hz, 1H), 3.52 (s, 3H), 4.39 (m, 1H), 6.63 (s, 1H), 6.75 (d, J=15.8 Hz, 1H), 7.21 (d, J=7.8 Hz, 2H), 7.34 (d, J=15.8 Hz, 1H), 7.43 (s, 1H), 7.45 (d, J=7.8 Hz, 2H), 8.03 (d, J=7.8 Hz, 1H).

Example 51

Production of N(α)-3-(4-methoxyphenyl)acryloyl-N(π)-methyl-L-histidine [Compound 17]

N(α)-3-(4-Methoxyphenyl)acryloyl-N(π)-methyl-L-histidine (1.9 g, 65%) was prepared as crystals by the same manner as in the production N(α)-3-(4-methylphenyl)acryloyl-N(π)-methyl-L-histidine starting from N(α)-3-(4-methoxyphenyl)acryloyl-N(π)-methyl-L-histidine methyl ester (3.0 g, 8.7 mmol), methanol (300 mL), a 1 mol/L aqueous solution of sodium hydroxide (13 mL, 13 mmol of NaOH), water (100 mL) and p-toluenesulfonic acid bead of a polystyrene bonding type (5.4 g, corresponding to 13 mmol of p-toluenesulfonic acid).

Mp. 145-146° C. $[α]_D^{20}$=+11.6° (c1, 0.1 mol/L NaOH). $^1$H-NMR DMSO-$d_6$ δ 2.95 (dd, J=8.4, 15.5 Hz, 1H), 3.08 (dd, J=4.9, 15.5 Hz, 1H), 3.55 (s, 3H), 3.78 (s, 3H), 4.59 (m, 1H), 6.59 (d, J=15.7 Hz, 1H), 6.68 (s, 1H), 6.97 (d, J=8.5 Hz, 2H), 7.37 (d, J=15.7 Hz, 1H), 7.51 (d, J=8.5 Hz, 2H), 7.52 (s, 1H), 8.31 (d, J=7.8 Hz, 1H).

Example 52

Production of N(α)-3-(4-chlorophenyl)acryloyl-N(π)-methyl-L-histidine [Compound 18]

N(α)-3-(4-Chlorophenyl)acryloyl-N(π)-methyl-L-histidine (4.0 g, 60%) was prepared as crystals by the same manner as in the production N(α)-3-(4-methylphenyl)acryloyl-N(π)-methyl-L-histidine starting from N(α)-3-(4-chlorophenyl)acryloyl-N(π)-methyl-L-histidine methyl ester (7.0 g, 20 mmol), methanol (300 mL), a 1 mol/L aqueous solution of sodium hydroxide (30 mL, 30 mmol of NaOH), water (100 mL) and p-toluenesulfonic acid bead of a polystyrene bonding type (12.7 g, corresponding to 30 mmol of p-toluenesulfonic acid).

Mp. 65-66° C. $[α]_D^{20}$=+8.3° (c1, 0.1 mol/L NaOH). $^1$H-NMR DMSO-$d_6$ δ 2.91 (dd, J=9.0, 14.9 Hz, 1H), 3.09 (dd, J=4.8, 14.9 Hz, 1H), 3.50 (s, 3H), 4.14 (m, 1H), 6.57 (s, 1H), 6.92 (d, J=15.8 Hz, 1H), 7.33 (d, J=15.8 Hz, 1H), 7.37 (s, 1H), 7.45 (d, J=8.3 Hz, 2H), 7.60 (d, J=8.3 Hz, 2H), 7.69 (d, J=7.8 Hz, 1H).

Example 53

Production of N(α)-3-(3,4-dichlorophenyl)acryloyl-N(π)-methyl-L-histidine [Compound 19]

N(α)-3-(3,4-Dichlorophenyl)acryloyl-N(π)-methyl-L-histidine (4.4 g, 59%) was prepared as crystals by the same manner as in the production N(α)-3-(4-methylphenyl)acryloyl-N(π)-methyl-L-histidine starting from N(α)-3-(3,4-dichloro-phenyl)acryloyl-N(π)-methyl-L-histidine methyl ester (7.5 g, 20 mmol), methanol (300 mL), a 1 mol/L aqueous solution of sodium hydroxide (30 mL, 30 mmol of NaOH), water (100 mL) and p-toluenesulfonic acid bead of a polystyrene bonding type (12.7 g, corresponding to 30 mmol of p-toluenesulfonic acid).

Mp. 170-171° C. $[α]_D^{20}$=+5.6° (c1, 0.1 mol/L NaOH). $^1$H-NMR DMSO-$d_6$ δ 2.97 (dd, J=8.1, 15.5 Hz, 1H), 3.10 (dd, J=4.8, 15.5 Hz, 1H), 3.55 (s, 3H), 4.56 (m, 1H), 6.68 (s, 1H), 6.85 (d, J=15.8 Hz, 1H), 7.40 (d, J=15.8 Hz, 1H), 7.51 (s, 1H), 7.56 (d, J=8.5 Hz, 1H), 7.67 (d, J=8.5 Hz, 1H), 7.85 (s, 1H), 8.35 (d, J=7.8 Hz, 1H).

Example 54

Production of N(α)-3-(4-fluorophenyl)acryloyl-N(π)-methyl-L-histidine [Compound 20]

N(α)-3-(4-Fluorophenyl)acryloyl-N(π)-methyl-L-histidine (4.8 g, 65%) was prepared as crystals by the same manner as in the production N(α)-3-(4-methylphenyl)acryloyl-N(π)-methyl-L-histidine starting from N(α)-3-(4-fluorophenyl)acryloyl-N(π)-methyl-L-histidine methyl ester (7.7 g, 20 mmol), methanol (300 mL), a 1 mol/L aqueous solution of sodium hydroxide (35 mL, 35 mmol of NaOH), water (100 mL) and p-toluenesulfonic acid bead of a polystyrene bonding type (14.8 g, corresponding to 35 mmol of p-toluenesulfonic acid).

Mp. 170-171° C. $[α]_D^{20}$=+15.3° (c1, 0.1 mol/L NaOH). $^1$H-NMR DMSO-$d_6$ δ 2.97 (dd, J=8.5, 15.5 Hz, 1H), 3.09 (dd, J=5.1, 15.5 Hz, 1H), 3.55 (s, H), 4.60 (m, 1H), 6.69 (s, 1H), 6.70 (d, J=15.8 Hz, 1H), 7.25 (m, 2H), 7.43 (d, J=15.8 Hz, 1H), 7.53 (s, 1H), 7.63 (m, 2H), 8.40 (d, J=7.8 Hz, 1H).

Example 55

Production of N(π)-3-(3,5-bistrifluoromethylphenyl)-acryloyl-N(π)-methyl-L-histidine [Compound 21]

N(α)-3-(3,5-Bistrifluoromethylphenyl)acryloyl-N(π)-methyl-L-histidine (2.8 g, 41%) was prepared as crystals by the same manner as in the production N(α)-3-(4-methylphenyl)acryloyl-N(π)-methyl-L-histidine starting from N(α)-3-(3,5-bistrifluoromethylphenyl)-acryloyl-N(π)-methyl-L-histidine methyl ester (7.0 g, 16 mmol), methanol (300 mL), a 1 mol/L aqueous solution of sodium hydroxide (24 mL, 24 mmol of NaOH), water (100 mL) and p-toluenesulfonic acid bead of a polystyrene bonding type (10.0 g, corresponding to 24 mmol of p-toluenesulfonic acid).

Mp. 215-216° C. $[α]_D^{20}$=+7.0° (c1, 0.1 mol/L NaOH). $^1$H-NMR DMSO-$d_6$ δ 2.99 (dd, J=8.4, 15.6 Hz, 1H), 3.11 (dd, J=5.0, 15.6 Hz, 1H), 3.55 (s, 3H), 4.62 (m, 1H), 6.70 (s, 1H), 7.07 (d, J=15.9 Hz, 1H), 7.53 (s, 1H), 7.61 (d, J=15.9 Hz, 1H), 8.09 (s, 1H), 8.28 (s, 2H), 8.42 (d, J=7.8 Hz, 1H).

Example 56

Production of N(α)-3-(4-isobutylphenyl)-acryloyl-N(π)-methyl-L-histidine [Compound 22]

N(α)-3-(4-Isobutylphenyl)-acryloyl-N(π)-methyl-L-histidine (4.7 g, 71%) was prepared as crystals by the same manner as in the production N(α)-3-(4-methylphenyl)acryloyl-N(π)-methyl-L-histidine starting from N(α)-3-(4-isobutylphenyl)-acryloyl-N(π)-methyl-L-histidine methyl ester (6.8 g, 18 mmol), methanol (300 mL), a 1 mol/L aqueous solution of sodium hydroxide (28 mL, 28 mmol of NaOH), water (100 mL) and p-toluenesulfonic acid bead of a polystyrene bonding type (11.6 g, corresponding to 28 mmol of p-toluenesulfonic acid).

Mp. 130-131° C. $[\alpha]_D^{20}$=+19.8° (c1, 0.1 mol/L NaOH).
$^1$H-NMR DMSO-$d_6$ δ 0.86 (d, J=6.6 Hz, 6H), 1.84 (m, 1H), 2.46 (d, J=6.9 Hz, 2H), 2.94 (dd, J=7.5, 15.3 Hz, 1H), 3.09 (dd, J=10.3, 15.3 Hz, 1H), 3.53 (s, 3H), 4.43 (m, 1H), 6.64 (s, 1H), 6.76 (d, J=15.8 Hz, 1H), 7.19 (d, J=7.8 Hz, 2H), 7.36 (d, J=15.8 Hz, 1H), 7.45 (s, 1H), 7.47 (d, J=7.8 Hz, 2H), 8.09 (d, J=7.8 Hz, 1H).

Example 57

Production of N(α)-3-(3,4-dimethoxyphenyl)acryloyl-N(π)-methyl-L-histidine [Compound 23]

N(α)-3-(3,4-Dimethoxyphenyl)-acryloyl-N(π)-methyl-L-histidine (3.7 g, 79%) was prepared as crystals by the same manner as in the production N(α)-3-(4-methylphenyl)acryloyl-N(π)-methyl-L-histidine starting from N(α)-3-(3,4-dimethoxyphenyl)-acryloyl-N(π)-methyl-L-histidine methyl ester (4.9 g, 13 mmol), methanol (300 mL), a 1 mol/L aqueous solution of sodium hydroxide (20 mL, 20 mmol of NaOH), water (100 mL) and p-toluenesulfonic acid bead of a polystyrene bonding type (8.3 g, corresponding to 20 mmol of p-toluenesulfonic acid).

Mp. 120-121° C. $[\alpha]_D^{20}$=+4.8° (c1, 0.1 mol/L NaOH).
$^1$H-NMR DMSO-$d_6$ δ 2.97 (dd, J=8.6, 15.6 Hz, 1H), 3.10 (dd, J=4.8, 15.6 Hz, 1H), 3.57 (s, 3H), 3.78 (s, 3H), 3.79 (s, 3H), 4.61 (m, 11-1), 6.63 (d, J=15.8 Hz, 1H), 6.75 (s, 1H), 6.98 (d, J=8.5 Hz, 1H), 7.11 (d, J=8.0 Hz, 1H), 7.16 (s, 1H), 7.36 (d, J=15.8 Hz, 1H), 7.64 s, 1H), 8.31 (d, J=7.8 Hz, 1H).

Example 58

Production of N(α)-3-(4-nitrophenyl)acryloyl-N(π)-methyl-L-histidine [Compound 24]

N(α)-3-(4-Nitrophenyl)-acryloyl-N(π)-methyl-L-histidine (3.7 g, 46%) was prepared as crystals by the same manner as in the production N(α)-3-(4-methylphenyl)acryloyl-N(π)-methyl-L-histidine starting from N(α)-3-(4-nitrophenyl)-acryloyl-N(π)-methyl-L-histidine methyl ester (8.4 g, 23 mmol), methanol (300 mL), a 1 mol/L aqueous solution of sodium hydroxide (35 mL, 35 mmol of NaOH), water (100 mL) and p-toluenesulfonic acid bead of a polystyrene bonding type (14.8 g, corresponding to 35 mmol of p-toluenesulfonic acid).

Mp. 225-226° C. $[\alpha]_D^{20}$+5.3° (c1, 0.1 mol/L NaOH).
$^1$H-NMR DMSO-$d_6$ δ 2.9 (dd, J=8.3, 15.5 Hz, 1H), 3.11 (dd, J=4.8, 15.5 Hz, 1H), 3.56 (s, 3H), 4.59 (m, 1H), 6.69 (s, 1H), 6.97 (d, J=15.4 Hz, 1H), 7.52 (s, 1H), 7.54 (d, J=15.4 Hz, 1H), 7.84 (d, J=8.7 Hz, 2H), 8.26 (d, J=8.7 Hz, 2H), 8.55 (d, J=7.8 Hz, 1H).

Example 59

Production of N(α)-3-(3-cyanophenyl)acryloyl-N(π)-methyl-L-histidine [Compound 25]

N(α)-3-(3-Cyanophenyl)-acryloyl-N(π)-methyl-L-histidine (4.1 g, 78%) was prepared as crystals by the same manner as in the production N(α)-3-(4-methylphenyl)acryloyl-N(π)-methyl-L-histidine starting from N(α)-3-(3-cyanophenyl)-acryloyl-N(π)-methyl-L-histidine methyl ester (5.0 g, 15 mmol), methanol (300 mL), a 1 mol/L aqueous solution of sodium hydroxide (23 mL, 23 mmol of NaOH), water (100 mL) and p-toluenesulfonic acid bead of a polystyrene bonding type (9.4 g, corresponding to 23 mmol of p-toluenesulfonic acid).

Mp. 180-181° C. $[\alpha]_D^{20}$=+11.8° (c1, 0.1 mol/L NaOH).
$^1$H-NMR DMSO-$d_6$ δ 2.95 (dd, J=7.2, 15.3 Hz, 1H), 3.10 (dd, J=4.8, 15.3 Hz, 1H), 3.52 (s, 3H), 4.36 (m, 1H), 6.63 (s, 1H), 6.98 (d, J=16.0 Hz, 1H), 7.41 (d, J=16.0 Hz, 1H), 7.44 (s, 1H), 7.61 (t, J=7.9, 7.9 Hz, 1H), 7.81 (d, J=7.9 Hz, 1H), 7.91 (d, J=7.9 Hz, 1H), 8.04 (d, J=7.8 Hz, 1H), 8.06 (s, 1H).

Example 60

Production of N(α)-3-(3-methoxyphenyl)acryloyl-N(π)-methyl-L-histidine [Compound 26]

N(α)-3-(3-Methoxyphenyl)-acryloyl-N(π)-methyl-L-histidine (4.3 g, 57%) was prepared as crystals by the same manner as in the production N(α)-3-(4-methylphenyl)acryloyl-N(π)-methyl-L-histidine starting from N(α)-3-(3-methoxyphenyl)-acryloyl-N(π)-methyl-L-histidine methyl ester (7.8 g, 23 mmol), methanol (300 mL), a 1 mol/L aqueous solution of sodium hydroxide (34 mL, 34 mmol of NaOH), water (100 mL) and p-toluenesulfonic acid bead of a polystyrene bonding type (14.4 g, corresponding to 34 mmol of p-toluenesulfonic acid).

Mp. 145-146° C. $[\alpha]_D^{20}$=+10.9° (c1, 0.1 mol/L NaOH).
$^1$H-NMR DMSO-$d_6$ δ 2.95 (dd, J=7.8, 15.4 Hz, 1H), 3.09 (dd, J=5.0, 15.4 Hz, 1H), 3.53 (s, 3H), 3.78 (s, 3H), 4.48 (m, 1H), 6.65 (s, 1H), 6.81 (d, J=16.0 Hz, 1H), 6.93 (m, 1H), 7.13 (s, 1H), 7.14 (m, 1H), 7.31 (m, 1H), 7.37 (d, J=16.0 Hz, 2H), 7.47 (s, 1H), 8.18 (d, J=7.8 Hz, 1H).

Example 61

Production of N(π)-benzyl-N(α)-tert-butoxycarbonyl-L-histidine methyl ester

N(α)-tert-Butoxycarbonyl-N(τ)-triphenylmethyl-L-histidine methyl ester (48.6 g, 95 mmol) was dissolved in methylene chloride (400 mL), benzyl bromide (13 mL, 110 mmol) was added thereto and the mixture was stirred for 48 hours and heated to reflux for 48 hours. Benzyl bromide (12 mL, 100 mmol) was further added thereto, the mixture was heated to reflux for 20 hours, benzyl bromide (12 mL, 100 mmol) was furthermore added thereto and the mixture was heated to reflux for 48 hours. The solvent was evaporated in vacuo, petroleum ether was added to the residue, the mixture was well stirred and allowed to stand and the supernatant liquid was discarded. The above operation was repeated for three times, the resulting oily residue (K) was dissolved in a 80% aqueous solution of acetic acid (300 mL), silver acetate (18.36 g, 110 mmol) was added thereto and the mixture was stirred at room temperature for 48 hours. After the insoluble matters were filtered off, the solvent was evaporated in vacuo and the resulting residue was dissolved again in water (400 mL). Potassium carbonate was added thereto to make it alkaline followed by extracting with ethyl acetate. The extract was washed with water and a saturated saline solution and dried over anhydrous sodium sulfate and the solvent was evaporated in vacuo. The residue was purified by a silica gel column chromatography (chloroform:methanol=9:1) to give N(π)-benzyl-N(α)-tert-butoxycarbonyl-L-histidine methyl ester (25.2 g, 74%) as crystals.

Mp. 123-124° C. $^1$H-NMR (DMSO-$d_6$) δ: 1.36 (s, 9H), 2.77 (dd, J=9.5, 15.5 Hz, 1H), 2.82 (dd, J=5.5, 15.5 Hz, 1H), 3.59 (s, 3H), 1.09-4.16 (m, 1H), 5.18 (s, 2H), 6.71 (s, 1H), 7.06-7.11 (m, 2H), 7.26-7.38 (m, 4H), 7.66 (s, 1H).

Example 62

Production of N(π)-4-chlorobenzyl-N(α)-tert-butoxy-carbonyl-L-histidine methyl ester N(π)-4-chlorobenzyl-N(α)-tert-butoxycarbonyl-L-histidine methyl ester (23.6 g, 63%) was prepared as an oily product by the same manner as in the production of N(π)-benzyl-N(α)-tert-butoxycarbonyl-L-histidine methyl ester starting from N(α)-tert-butoxycarbonyl-N(τ)-triphenyl-methyl-L-histidine methyl ester (48.6 g, 95 mmol), 4-chlorobenzyl bromide (50 g, 244 mmol), a 80% aqueous solution of acetic acid (300 mL) and silver acetate (16.70 g, 100 mmol).

$^1$H-NMR (DMSO-$d_6$) δ: 1.35 (s, 9H), 2.76 (dd, J=9.6, 15.5 Hz, 1), 2.82 (dd, J=5.1, 15.5 Hz, 1H), 3.59 (s, 3H), 4.07-4.15 (m, 1H), 5.19 (s, 2H), 6.72 (s, 1H), 7.10 (d, J=8.4 Hz, 2H), 7.34 (d, J=8.1 Hz, 1H), 7.41 (d, J=8.4 Hz, 2H), 7.68 (s, 1H).

Example 63

Production of N(π)-4-methylbenzyl-N(α)-tert-butoxy-carbonyl-L-histidine methyl ester N(π)-4-methylbenzyl-N(α)-tert-butoxycarbonyl-L-histidine methyl ester (25.37 g, 74%) was produced as an oily product by the same manner as in the production of N(π)-benzyl-N(α)-tert-butoxycarbonyl-L-histidine methyl ester starting from N(α)-tert-butoxycarbonyl-N(τ)-triphenyl-methyl-L-histidine methyl ester (48.6 g, 95 mmol), 4-methylbenzyl bromide (25 g, 135 mmol), a 80% aqueous solution of acetic acid (300 mL) and silver acetate (16.70 g, 100 mmol).

$^1$H-NMR (DMSO-$d_6$) δ: 1.36 (s, 9H), 2.27 (s, 3H), 2.76 (dd, J=9.6, 15.5 Hz, 1H), 2.82 (dd, J=5.2, 15.5 Hz, 1H), 3.59 (s, 3H), 4.08-4.16 (m, 1H), 5.12 (s, 2H), 6.69 (s, 1H), 6.99 (d, J=7.9 Hz, 2H), 7.14 (d, J=7.9 Hz, 2H), 7.35 (d, J=8.1 Hz, 1H), 7.64 (s, 1H).

Example 64

Production of N(π)-benzyl-L-histidine methyl ester dihydrochloride

N(π)-Benzyl-N(α)-tert-butoxycarbonyl-L-histidine methyl ester (22.0 g, 61 mmol) was dissolved in methylene chloride (200 mL) and a 4 mol/L solution of hydrogen chloride in dioxane (100 mL, 400 mmol HCl) was dropped thereinto at room temperature. After stirring for 6 hours, the solvent was evaporated therefrom in vacuo and the resulting oily residue was solidified with petroleum ether to give N(π)-benzyl-L-histidine methyl ester dihydrochloride (24.15 g, quantitatively) as an amorphous solid.

$^1$H-NMR (DMSO-$d_6$) δ: 3.19 (dd, J=7.5, 16.2 Hz, 1H), 3.32 (dd, J=7.2, 16.2 Hz, 1H), 3.69 (s, 3H), 3.88 (dd, J=7.2, 7.5 Hz, 1H), 5.40 (s, 2H), 7.23-7.26 (m, 2H), 7.37-7.43 (m, 3H), 8.76 (s, 1H).

Example 65

Production of N(π)-4-chlorobenzyl-L-histidine methyl ester dihydrochloride

N(π)-4-Chlorobenzyl-L-histidine methyl ester dihydrochloride (17.47 g, 79%) was prepared as crystals by the same manner as in the production of N(π)-benzyl-L-histidine methyl ester dihydrochloride starting from N(π)-4-chlorobenzyl-N(α)-tert-butoxycarbonyl-L-histidine methyl ester (23.6 g, 60 mmol), a 4 mol/L solution of hydrogen chloride in dioxane (150 mL, 600 mmol HCl) and methylene chloride (200 mL).

Mp. 153-155° C. $^1$H-NMR (DMSO-$d_6$) δ: 3.21 (dd, J=6.5, 16.0 Hz, 1H), 3.28 (dd, J=7.1, 16.0 Hz, 1H), 3.73 (s, 3H), 4.32 (dd, J=6.5, 7.1 Hz, 1H), 5.58 (s, 2H), 7.40 (d, J=8.4 Hz, 2H), 7.50 (d, J=8.4 Hz, 2H), 7.65 (s, 1H), 8.80-9.20 (brs, 3H), 9.26 (s, 1H), 14.50-15.50 (brs, 1H).

Example 66

Production of N(π)-4-methylbenzyl-L-histidine methyl ester dihydrochloride

N(π)-4-Methylbenzyl-L-histidine methyl ester dihydrochloride (17.45 g, 75%) was prepared as crystals by the same manner as in the production of N(π)-benzyl-L-histidine methyl ester dihydrochloride starting from N(π)-4-methylbenzyl-N(α)-tert-butoxycarbonyl-L-histidine methyl ester (25.0 g, 67 mmol), a 4 mol/L solution of hydrogen chloride in dioxane (150 mL, 600 mmol HCl) and methylene chloride (200 mL).

Mp. 143-144° C. $^1$H-NMR (DMSO-$d_6$) δ: 2.31 (s, 3H), 3.20 (dd, J=6.6, 16.0, 1H), 3.26 (dd, J=7.1, 16.0, 1H), 3.73 (s, 3H), 4.31 (dd, J=6.6, 7.1 Hz, 1H), 5.49 (s, 2H), 7.32 (s, 4H), 7.63 (s, 1H), 8.80-9.10 (brs, 3H), 9.20 (s, 1H), 14.5-15.5 (brs, 1H).

Example 67

Production of N(α)-acryloyl-N(π)-benzyl-L-histidine methyl ester

N(π)-Benzyl-L-histidine methyl ester dihydrochloride (24.15 g, 60 mmol) was dissolved in methylene chloride (500 mL) and, after acrylic acid (4.5 mL, 66 mmol) and triethylamine (21 mL, 150 mmol) were added thereto, a solution of DCC (13.6 g, 66 mmol) in methylene chloride (50 mL) was dropped thereinto at room temperature. After stirring at room temperature for 48 hours, the insoluble matters therein were filtered off and the solvent of the filtrate was evaporated in vacuo. The oily residue was spread on a column filled with silica gel BW-127 ZH for normal phase chromatography and eluted with chloroform:methanol (19:1) to give N(α)-acryloyl-N(π)-benzyl-L-histidine methyl ester (4.70 g, 25%) as an oily product.

$^1$H-NMR (DMSO-$d_6$) δ: 2.84 (dd, J=8.5, 15.5 Hz, 1H), 2.91 (dd, J=5.5, 15.5 Hz, 1H), 3.60 (s, 3H), 4.46-4.51 (m, 1H), 5.17 and 5.19 (ABq, J=16.1 Hz, 2H), 5.63 (dd, J=2.0, 10.2 Hz, 1H), 6.10 (dd, J=2.0, 17.2 Hz, 1H), 6.26 (dd, J=10.2, 17.2 Hz, 1H), 6.70 (s, 1H), 7.06-7.11 (m, 2H), 7.26-7.38 (m, 3H), 7.67 (s, 1H), 8.61 (d, J=7.7 Hz, 1H).

Example 68

Production of N(α)-acryloyl-N(π)-4-chlorobenzyl-L-histidine methyl ester

N(α)-acryloyl-N(π)-4-chlorobenzyl-L-histidine methyl ester (9.21 g, 56%) was prepared as an oily product by the same manner as in the production of N-(α)-acryloyl-N(π)-benzyl-L-histidine methyl ester starting from N(π)-4-chlorobenzyl-L-histidine methyl ester dihydrochloride (17.23 g, 47 mmol), acrylic acid (3.8 mL, 35 mmol), triethylamine (23 mL, 165 mmol), DCC (11.35 g, 55 mmol) and methylene chloride (600 mL).
$^1$H-NMR (DMSO-d$_6$) δ: 2.83 (dd, J=9.0, 15.6, 1H), 2.90 (dd, J=5.5, 15.6 Hz, 1H), 3.60 (s, 3H), 4.46-4.72 (m, 1H), 5.18 and 5.22 (ABq, J=16.3 Hz, 2H), 5.63 (dd, J=2.0, 10.2 Hz, 1H), 6.19 (dd, J=2.0, 17.1 Hz, 1H), 6.25 (dd, J=10.2, 17.1 Hz, 1H), 6.70 (s, 1H), 7.10 (d, J=8.4 Hz, 2H), 7.42 (d, J=8.4 Hz, 2H), 7.69 (s, 1H), 8.62 (d, J=7.8 Hz, 1H).

Example 69

Production of N(α)-acryloyl-N(π)-4-methylbenzyl-L-histidine methyl ester

N(α)-Acryloyl-N(π)-4-methylbenzyl-L-histidine methyl ester (7.48 g, 47%) was prepared as an oily product by the same manner as in the production of N-(α)-acryloyl-N(π)-benzyl-L-histidine methyl ester starting from N(π)-4-methylbenzyl-L-histidine methyl ester dihydrochloride (17.0 g, 49 mmol), acrylic acid (3.8 mL, 35 mmol), triethylamine (23 mL, 165 mmol), DCC (11.35 g, 55 mmol) and methylene chloride (600 mL).
$^1$H-NMR (DMSO-d$_6$) δ: 2.27 (s, 3H), 2.83 (dd, J=8.7, 15.6 Hz, 1H), 2.90 (dd, J=5.5, 15.6 Hz, 1H), 3.60 (s, 3H), 4.47-4.53 (m, 1H), 5.10 and 5.14 (ABq, J=15.9 Hz, 2H), 5.63 (dd, J=2.0, 10.2 Hz, 1H), 6.10 (dd, J=2.0, 17.1 Hz, 1H), 6.26 (dd, J=10.2, 17.1 Hz, 1H), 6.68 (s, 1H), 6.99 (d, J=7.9 Hz, 2H), 7.16 (d, J=7.9 Hz, 2H), 7.56 (s, 1H), 8.61 (d, J=7.7 Hz, 1H).

Example 70

Production of N(α)-acryloyl-N(π)-benzyl-L-histidine [Compound 27]

N(α)-Acryloyl-N(π)-benzyl-L-histidine methyl ester (4.39 g, 14%) was dissolved in methanol (120 mL) and a 1 mol/L aqueous solution of sodium hydroxide (17 mL, 17 mmol of NaOH) was added thereto at room temperature. After stirring for 30 minutes, the solvent thereof was evaporated in vacuo, the residue was dissolved in water and beads of p-toluenesulfonic acid of a polystyrene bonding type (6.0 g, corresponding to 18 mmol of p-toluenesulfonic acid) were added thereto. After confirming its pH was 7, the beads were filtered off and the filtrate was filtered through a membrane filter of 0.45 μm. When the filtrate was evaporated in vacuo, crystals were separated out. The crystals were dried, ether was added thereto and the mixture was filtered and dried on phosphorus pentaoxide in vacuo at room temperature for 48 hours to give N(α)-acryloyl-N(π)-benzyl-L-histidine (3.28 g, 78%).
Mp. 192-194° C. $[α]_D^{20}$=□26.1° (c1, 0.1 mol/L NaOH). $^1$H-NMR (0.1 mol/L NaOD) δ: 2.76 (dd, J=8.3, 15.7 Hz, 1H), 2.91 (dd, J=4.8, 15.7 Hz, 1H), 4.22-4.27 (m, 1H), 5.03 and 5.06 (ABq, J=16.1 Hz, 2H), 5.59 (dd, J=1.2, 10.1 Hz, 1H), 5.98 (dd, J=1.2, 17.2 Hz, 1H), 6.06 (dd, J=10.1, 17.2 Hz, 1H), 6.70 (s, 1H), 6.96-7.01 (m, 2H), 7.18-7.27 (m, 3H), 7.53 (s, 1H).

Example 71

Production of N(α)-acryloyl-N(π)-4-chlorobenzyl-L-histidine [Compound 28]

N(α)-Acryloyl-N(π)-4-chlorobenzyl-L-histidine (6.18 g, 71%) was prepared by the same manner as in the production of N(α)-acryloyl-N(π)-benzyl-L-histidine starting from N(α)-acryloyl-N(π)-chlorobenzyl-L-histidine methyl ester (9.04 g, 26 mmol), a 1 mol/N aqueous solution of sodium hydroxide (40 mL, 40 mmol of NaOH), methanol (260 mL) and beads of p-toluenesulfonic acid of a polystyrene bonding type (18.0 g, corresponding to 43 mmol of p-toluenesulfonic acid).
Mp. 120° C.□decomp.□. $[α]_D^{20}$=□25.0° (c1, DMF). $^1$H-NMR (DMSO-d$_6$) δ: 2.78 (dd, J=8.1, 15.5 Hz, 1H), 2.90 (dd, J=4.8, 15.5 Hz, 1H), 4.36-4.40 (m, 1H), 5.15 and 5.22 (ABq, J=16.2 Hz, 2H), 5.57 (dd, J=2.0, 10.2 Hz, 1H), 6.07 (dd, J=2.0, 17.0 Hz, 1H), 6.32 (dd, J=10.2, 17.0 Hz, 1H), 6.69 (s, 1H), 7.11 (d, J=8.4 Hz, 2H), 7.39 (d, J=8.4 Hz, 2H), 7.64 (s, 1H), 8.24 (d, J=7.9 Hz, 1H).

Example 72

Production of N(α)-acryloyl-N(π)-4-methylbenzyl-L-histidine [Compound 29]

N(α)-Acryloyl-N(π)-4-methylbenzyl-L-histidine (3.91 g, 57%) was prepared by the same manner as in the production of N(α)-acryloyl-N(π)-benzyl-L-histidine starting from N(α)-acryloyl-N(π)-methylbenzyl-L-histidine methyl ester (7.20 g, 22 mmol), a 1 mol/N aqueous solution of sodium hydroxide (30 mL, 30 mmol of NaOH), methanol (250 mL) and beads of p-toluenesulfonic acid of a polystyrene bonding type (14.0 g, corresponding to 33 mmol of p-toluenesulfonic acid).
Mp. 117-119° C. $[α]_D^{20}$=□19.3° (c1, DMF). $^1$H-NMR (DMSO-d$_6$) δ: 2.27 (s, 3H), 2.79 (dd, J=8.3, 15.5 Hz, 1H), 2.90 (dd, J=4.9, 15.5 Hz, 1H), 4.17-4.43 (m, 1H), 5.08 and 5.14 (ABq, J=15.8 Hz, 2H), 5.88 (dd, J=2.0, 10.2 Hz, 1H), 6.07 (dd, J=2.0, 17.0 Hz, 1H), 6.30 (dd, J=10.2, 17.0 Hz, 1H), 6.67 (s, 1H), 6.99 (d, J=7.9 Hz, 2H), 7.14 (d, J=7.9 Hz, 2H), 7.61 (s, 1H), 8.29 (d, J=7.9 Hz, 1H).

Example 73

Production of N(α)-methacryl-N(π)-methyl-L-histidine methyl ester

N(π)-Methyl-L-histidine methyl ester trihydrochloride (10.55 g, 36 mmol), triethylamine (22 mL, 156 mmol) and methacrylic acid (3.4 mL, 40 mmol) were dissolved in methylene chloride (500 mL) and a solution of DCC (8.25 g, 40 mmol) in methylene chloride (50 mL) was dropped thereinto at room temperature. After stirring the above at room temperature for 48 hours, the insoluble matters were filtered off and the solvent of the filtrate was evaporated in vacuo. The oily residue was spread on a column filled with silica gel BW-127 ZH for normal phase chromatography and eluted with chloroform:methanol (19:1) to give N(α)-methacryl-N(π)-methyl-L-histidine methyl ester (1.53 g, 17%) as crystals.

Mp. 74-76° C. $^1$H-NMR (DMSO-$d_6$) δ: 1.82 (s, 3H), 3.03 (dd, J=9.6, 15.4 Hz, 1H), 3.08 (dd, J=5.5, 15.4 Hz, 1H), 3.54 (s, 3H), 3.63 (s, 3H), 4.49-4.55 (m, 1H), 5.38 (s, 1H), 5.66 (s, 1H), 6.63 (s, 1H), 7.48 (s, 1H), 8.31 (d, J=7.8 Hz, 1H).

Example 74

Production of N(α)-methacryl-N(π)-methyl-L-histidine [Compound 30]

N(α)-Methacryl-N(π)-methyl-L-histidine methyl ester (1.40 g, 5.6 mmol) was dissolved in methanol (70 mL) and a 1 mol/L aqueous solution of sodium hydroxide (7.0 mL, 7.0 mmol of NaOH) was added thereto at room temperature. After stirring the above at room temperature for 30 minutes, the solvent was evaporated therefrom in vacuo. The residue was dissolved in water (50 mL) and beads of p-toluenesulfonic acid of a polystyrene bonding type (2.5 g, corresponding to 7.5 mmol of p-toluenesulfonic acid) were added thereto. When its pH was confirmed to be 7, the beads were filtered off and the filtrate was filtered through a membrane filter of 0.45 μm. The filtrate was freeze-dried to give N(α)-methacryl-N(π)-methyl-L-histidine (1.26 g, 95%) as a hygroscopic amorphous solid.

$[α]_D^{20}$=012.3° (c1, 0.1 mol/L NaOH). $^1$H NMR (0.1 mol/L NaOD) δ: 1.74 (s, 3H), 2.90 (dd, J=8.9, 15.5 Hz, 1H), 3.08 (dd, J=4.9, 15.5 Hz, 1H), 3.49 (s, 3H), 4.37 (dd, J=4.9, 8.9 Hz, 1H), 5.29 (s, 1H), 5.49 (s, 1H), 6.63 (s, 1H), 7.41 (s, 1H).

Example 75

Test for Analgesic Effect (1)

In a test for analgesic effect, a pathological animal model called SART stressed mouse which shows a chronic hyperalgesia state was used. Loading of SART (Specific Alternation of Rhythm in Temperature) stress or repetitive cold stress was conducted in accordance with a method of Kita, et al. (*Nippon Yakurigaku Zasshi*, Vol. 71, pages 195 to 210, 1975). In a constant-temperature vessel for breeding, a breeding environment temperature for male mice of ddY strain was alternately changed at 4° C. and 24° C. every one hour from 10 a.m. until 5 p.m. and kept at 4° C. from 5 p.m. to 10 a.m. of the next morning. Breeding was conducted for 5 days where water and feed were freely taken by the mice so as to load a repetitive cold stress and, after that, the mice were subjected to the test. Before and after 30 minutes from administration of the test substance, analgesic threshold value was measured by a modified Randall-Selitto method (Tail pressure method; *Nippon Yakurigaku Zasshi*, Vol. 72, pages 573 to 584, 1976). Thus, Using a Randall-Selitto analgesic effect measuring device where a pressing piece was modified for mouse tail, a pressure stimulation was applied at the rate of 16 g/second to the site which was 1.5 cm to the front end from tail root of the mouse and pressurized weight (g) showing an escaping or squeaking reaction was measured and adopted as a pain threshold value. In a normal control group, the pain threshold value was about 125 to 135 g while, in the SART control group to which SART stress was loaded, pain reaction was noted at the pressurized weight (pain threshold value) of about 80 to 85 g whereby the SART stressed mice were in hyperalgesia. A value (analgesic coefficient) where the pain threshold of the test substance administration group was divided by the pain threshold of the SART control group was calculated and the analgesic effect of the test substance was confirmed. Thus, when the test substance had no effect at all, said value was 1.0 and, as the effect became stronger, the value of the analgesic coefficient increased as 1.1, 1.2 and 1.3. Significant difference between the two groups was determined by a statistic processing of the pain threshold values and the analgesic coefficient was calculated as a mean value of the pain threshold values.

As to the test animals, male mice of ddY strain of four weeks age (one group comprised ten mice) were used. The compound of the present invention as a test substance was administered at a dose of 25 ng or 50 ng per mouse into the lateral ventricle whereupon its analgesic effect was measured. An example (mean value of the analgesic coefficients) of the result of the above test is shown in Table 1. When an analgesic effect test using the SART stressed mouse which is pathologic model animal showing chronic hyperalgesia was conducted, the compounds of the present invention showed an excellent analgesic effect. In a significance test for pain threshold values, Dunnett's multiple comparison test was used and the result in the test substances in the table showed a significant difference in $p<0.05$ as compared with the SART stressed mouse control group in any case.

TABLE 1

| Test substance | Dose (ng) | Analgesic coefficient |
|---|---|---|
| Compound 1 | 25 | 1.33 |
| Compound 3 | 25 | 1.23 |
| Compound 6 | 25 | 1.17 |
| Compound 7 | 25 | 1.31 |
| Compound 10 | 25 | 1.14 |
| Compound 2 | 50 | 1.18 |
| Compound 13 | 50 | 1.31 |

Further, when the Compound 1 of the present invention was intraperitoneally administered (100 μg/kg), the pain threshold value in the SART control group was 79.0 kg while, in the test substance administration group, it was 97.8 g (analgesic coefficient: 1.24) whereby a significant improving effect for hyperalgesia was noted. In the case of oral administration, a significant analgesic action was showed at a dose of 3 and 10 mg/kg having a peak after 30 minutes from the oral administration and $ED_{50}$ value determined from the improving rate upon the action was in peak was 2.7 mg/kg. On the contrary, when an analgesic test was conducted for anserine and carnosine as test substances by the above-mentioned administration into the lateral ventricle, no significant analgesic action was found.

Example 76

Test for Analgesic Effect (2)

A test for analgesic effect was conducted using a Chung model rat which is a neuropathic pain model. As to the test animal, male rats of Wistar strain of nine weeks age were used and model rats were prepared in accordance with the method of Kim and Chung (*Pain*, vol. 50, pages 355 to 363, 1992). Thus, under anesthetization with pentobarbital (40 mg/kg, intraperitoneal administration), rat L5 spinal nerve was exposed and L5 dorsal root ganglion periphery side was strongly ligated using 5-0 silk yarn. The animals were placed in a transparent acrylate cage whose bottom was made of wire net, a 50% reaction threshold value was calculated by an up-down method using a von Frey filament (manufactured by North Coast Medical Inc.) according to the methods of Chaplan, et al. (*J. Neurosci. Method*, vol. 53, pages 55 to 63, 1994) and by Lee, et al. (*J. Neurophysiol.*, vol. 81, pages 2226 to 2233, 1999) and measurement of allodynia was conducted. Before injury of spinal nerve, the 50% reaction threshold value was measured twice and the animals where the threshold value was outside the standard were excluded from the operation for spinal nerve injury. After 14, 17 and 28 days from the spinal nerve injury, the 50% reaction threshold values were measured and the animals which showed a stable decrease in the threshold and also showed a threshold of 1 g to less than 4 g after 28 days were used for the test. Those test animals were made into groups of seven animals so that the mean value of 50% reaction threshold after 28 days from the nerve injury as an index became nearly the same in each group.

The Compound 1 of the present invention as a test substance was intraperitoneally administered (100 μg/kg) in a single dose while, a 0.5% CMC-Na/physiological saline solution was administered similarly to a nerve injury control group. After 30 minutes from the administration of the test substance, allodynia was measured to calculate a 50% reaction threshold value. With regard to a significance test, Paired t-test was conducted for comparison between before and after the nerve injury and Dunnett's multiple comparison test was used for comparison among multiple groups of the nerve injury control group and the test substance administration group. In any of the cases, the results showed significant difference in p<0.05.

As a result of the above analgesic effect test, the mean value of 50% reaction threshold at the normal stage before the L5 spinal nerve injury was 15.00 g (n=42) while, after 28 days from the nerve injury, it lowered to 2.46 g (n=42; before constituting the group). As the result of 50% reaction threshold value before and after the spinal nerve injury, it was confirmed that a mechanical allodynia was obviously occurred. On the basis of above confirmation, when an analgesic effect test of the compounds of the present invention using Chung model rats was carried out, the mean value of 50% reaction threshold in the nerve injury control group was 2.48 (n=7, after constituting the group) before administration of the solvent while, after 30 minutes from the administration of the solvent, it was 2.70 g whereby no big change was observed between the stages before and after the administration. On the contrary, the 50% reaction threshold value of the test substance administration group was 9.60 g showing a significant increase in the threshold as compared with the nerve injury control group. Accordingly, a strong anti-allodynia action of the compound of the present invention or an excellent analgesic action to neuropathic pain was observed. In the case of oral administration, the Compound 1 of the present invention showed a significant anti-allodynia action to a mechanical allodynia of Chung's model rats at the dose of 10 mg/kg having a peak after 30 minutes from the oral administration, and the $ED_{50}$ value determined from the improving rate at the peak of the action was 2.4 mg/kg.

Example 77

Test for Analgesic Effect (3)

In the same manner as in the above test for analgesic effect (2), the Compounds 2, 6, 7, 27 and 30 of the present invention as test substances were intraperitoneally administered (400 μg/kg) in a single dose while, to the neuropathic injury control group, a 0.5% CMC-Na/physiological saline solution was administered similarly. After 30 minutes from administration of the test substance, measurement of allodynia was conducted to calculate the 50% reaction threshold value. An example of the test result is shown in Table 2. When an analgesic effect test using Chung model rats which is a neuropathic pain model was conducted, the compounds of the present invention showed a significantly excellent analgesic effect.

TABLE 2

| | 50% reaction threshold value (g) | | | |
|---|---|---|---|---|
| | Nerve injury control group | | Test substance administration group | |
| Test substance | Before admin. | After admin. for 30 minutes | Before admin. | After admin. for 30 minutes |
| Compound 2 | 2.68 ± 0.25 | 3.86 ± 0.38 | 2.69 ± 0.39 | 5.98 ± 0.52* |
| Compound 6 | 2.67 ± 0.24 | 3.27 ± 0.30 | 2.69 ± 0.33 | 6.43 ± 1.52* |
| Compound 7 | 2.68 ± 0.25 | 3.86 ± 0.38 | 2.71 ± 0.24 | 9.88 ± 1.59* |
| Compound 27 | 2.61 ± 0.25 | 2.81 ± 0.38 | 2.58 ± 0.26 | 7.32 ± 1.32* |
| Compound 30 | 2.61 ± 0.25 | 2.81 ± 0.38 | 2.63 ± 0.23 | 4.30 ± 0.46* |

*P<0.05 (Dunnett's multiple comparison test)

Example 78

Test for Analgesic Effect (4)

The compounds of the present invention were orally administered to mice and a test for an analgesic effect was carried out by means of an acetic acid writhing test. As to the test animals, male mice of ddY strain of four weeks age were subjected to a preliminary breeding and they were used where one group comprised ten mice. Each of the compound of the present invention as a test substance was orally administered (10 mg/kg, 100 mg/kg) in a single dose while, to a control group, distilled water (water for injection) was administered similarly. After 25 minutes from the administration of the test substance, a 0.7% acetic acid/physiological saline was intraperitoneally administered at the dose of 10 mL/kg. From 5 minutes thereafter, writhing numbers during 10 minutes were counted and a suppressive rate for each mouse was calculated according to the following formula.

Suppressive Rate(%)=[(Mean writhing numbers of the control group)−(Writhing numbers of each mouse)]÷[Mean writhing numbers of the control group]×100

An example of the result of the above test is shown in Table 3. When a test for analgesic effect by an acetic acid writhing test was conducted, the compounds of the present invention showed an excellent analgesic effect.

TABLE 3

| Test substance | Dose (mg/kg) | Suppressive Rate (%) |
|---|---|---|
| Compound 1 | 10 | 33.1 |
| | 100 | 53.8 |
| Compound 2 | 100 | 27.6 |
| Compound 4 | 10 | 32.9 |
| Compound 5 | 10 | 17.8 |
| Compound 6 | 100 | 23.5 |
| Compound 7 | 100 | 36.1 |
| Compound 9 | 100 | 38.0 |
| Compound 10 | 10 | 27.7 |
| Compound 11 | 10 | 36.1 |
| Compound 16 | 100 | 30.3 |
| Compound 27 | 10 | 37.9 |

Besides the above-mentioned acetic acid writhing test, the Compound 1 showed a significant analgesic action by oral administration of 100 mg/kg against a pain reaction in the second phase of a formalin pain test for rats. For hyperalgesia in osteoarthritis model induced by administration of monoiodoacetic acid into joints of rats, oral administration of 1 mg/kg of the Compound 1 also showed a significant analgesic effect.

Example 79

Single Dose Toxicity Test by Administration to Mice

A single dose toxicity test by intraperitoneal administration of the compounds of the present invention to mice was carried out. Male mice of ddY strain of four weeks age were made into groups of five mice so as to make mean body weight in each group nearly the same. The Compound 1 of the present invention as a test substance was intraperitoneally administered at the doses of 250 mg/kg, 500 mg/kg and 1,000 mg/kg.

In this toxicity test, no abnormal observation was noted during the observation period from initial administration until 14 days after the administration in any of the doses and no death case was noted as well. Further, after finishing the observation period for 14 days, autopsied organs and tissues of the body were observed by naked eye whereupon no abnormal case was found at all as in the case of the control group (group to which a physiological saline was administered). With regard to changes in the body weight, no significant difference was also noted at all as compared with the control group. From those results, it was found that the compounds of the present invention showed no toxic affection at all by intraperitoneal administration to mice and were very low toxicity.

As shown in the above-mentioned various tests for an analgesic effect, the histidine derivative of the present invention shows an excellent analgesic action to pathogenic model animals for acute or chronic pain and neuropathic pain and is very low toxicity. Accordingly, the compound of the present invention is very useful as a pharmaceutical agent for the treatment of various kinds of acute or chronic pain diseases and of neuropathic pain diseases such as reflex sympathetic dystrophy, postherpetic neuralgia and diabetic neuropathy which are hardly curable by common analgesic such as non-steroidal anti-inflammatory drugs (NSAIDs).

The invention claimed is:

1. A histidine derivative represented by the following formula (I) or a pharmaceutically acceptable salt or hydrate thereof,

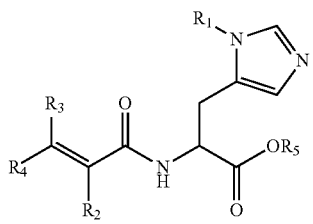
(I)

wherein: $R_1$ is alkyl having 1 to 6 carbon(s) or benzyl which may be substituted with alkyl having 1 to 4 carbon(s) or halogen; $R_2$ is hydrogen or alkyl having 1 to 4 carbon(s); $R_3$ and $R_4$ are same or different and each is hydrogen, alkyl having 1 to 4 carbon(s) or phenyl which may be substituted with any one or two of alkyl having 1 to 6 carbon(s), alkoxy having 1 to 6 carbon(s), halogen, trifluoromethyl, nitro and cyano; and $R_5$ is hydrogen or an alkyl group having 1 to 4 carbon(s).

2. The histidine derivative or a pharmaceutically acceptable salt or hydrate thereof according to claim 1, wherein $R_1$ is alkyl having 1 to 6 carbon(s).

3. The histidine derivative or a pharmaceutically acceptable salt or hydrate thereof according to claim 2, wherein $R_3$ is hydrogen.

4. The histidine derivative or a pharmaceutically acceptable salt or hydrate thereof according to claim 3, wherein $R_4$ is hydrogen.

5. The histidine derivative or a pharmaceutically acceptable salt or hydrate thereof according to claim 3, wherein $R_4$ is alkyl having 1 to 4 carbon(s).

6. The histidine derivative or a pharmaceutically acceptable salt or hydrate thereof according to claim 3, wherein $R_4$ is phenyl.

7. The histidine derivative or a pharmaceutically acceptable salt or hydrate thereof according to claim 4, wherein $R_2$ is hydrogen.

8. The histidine derivative or a pharmaceutically acceptable salt or hydrate thereof according to claim 4, wherein $R_2$ is alkyl having 1 to 4 carbon(s).

9. The histidine derivative or a pharmaceutically acceptable salt or hydrate thereof according to claim 1, wherein $R_1$ is benzyl and $R_2$, $R_3$ and $R_4$ are hydrogen.

10. N($\alpha$)-acryloyl-N($\pi$)-methyl-L-histidine, N($\alpha$)-acryloyl-N($\pi$)-ethyl-L-histidine, N($\alpha$)-crotonoyl-N($\pi$)-methyl-L-histidine, N($\alpha$)-3-phenylpropenoyl-N($\pi$)-methyl-L-histidine, N($\alpha$)-2-methyl-2-butenoyl-N($\pi$)-methyl-L-histidine, N($\alpha$)-3-phenylpropenoyl-N($\pi$)-ethyl-L-histidine, N($\alpha$)-acryloyl-N($\pi$)-isopropyl-L-histidine, N($\alpha$)-acryloyl-N($\pi$)-benzyl-L-histidine, N($\alpha$)-methacryl-N($\pi$)-methyl-L-histidine or a pharmaceutically acceptable salt or hydrate thereof.

11. N($\alpha$)-acryloyl-N($\pi$)-methyl-L-histidine or a pharmaceutically acceptable salt or hydrate thereof.

12. A pharmaceutical preparation comprising the histidine derivative represented by the following formula (I) or a pharmaceutically acceptable salt or hydrate thereof,

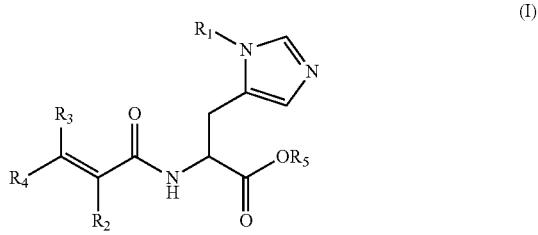
(I)

wherein: $R_1$ is alkyl having 1 to 6 carbon(s) or benzyl which may be substituted with alkyl having 1 to 4 carbon(s) or halogen; $R_2$ is hydrogen or alkyl having 1 to 4 carbon(s); $R_3$ and $R_4$ are same or different and each is hydrogen, alkyl having 1 to 4 carbon(s) or phenyl which may be substituted with any one or two of alkyl having 1 to 6 carbon(s), alkoxy having 1 to 6 carbon(s), halogen, trifluoromethyl, nitro and cyano; and $R_5$ is hydrogen or an alkyl group having 1 to 4 carbon(s) and a pharmaceutical carrier or diluent.

13. A pharmaceutical preparation comprising N(α)-acryloyl-N(π)-methyl-L-histidine, N(α)-acryloyl-N(π)-ethyl-L-histidine, N(α)-crotonoyl-N(π)-methyl-L-histidine, N(α)-3-phenylpropenoyl-N(π)-methyl-L-histidine, N(α)-2-methyl-2-butenoyl-N(π)-methyl-L-histidine, N(α)-3-phenylpropenoyl-N(π)-ethyl-L-histidine, N(α)-acryloyl-N(π)-isopropyl-L-histidine, N(α)-acryloyl-N(π)-benzyl-L-histidine, N(α)-methacryl-N(π)-methyl-L-histidine or a pharmaceutically acceptable salt, ester or hydrate thereof and a pharmaceutical carrier or diluent.

14. A pharmaceutical preparation comprising N(α)-acryloyl-N(π)-methyl-L-histidine or a pharmaceutically acceptable salt, ester or hydrate thereof.

15. The pharmaceutical preparation according to claim 12 wherein said histidine derivative is an analgesic and the preparation is in the form of a tablet, capsule, powder or liquid.

16. A pharmaceutically acceptable salt of the histidine derivative according to claim 1.

17. A hydrate of the histidine derivative according to claim 1.

\* \* \* \* \*